US010344035B2

(12) United States Patent
Yu et al.

(10) Patent No.: US 10,344,035 B2
(45) Date of Patent: Jul. 9, 2019

(54) SALT OF QUINOLONE COMPOUND, POLYMORPHS THEREOF, PREPARATION METHOD THEREFOR, COMPOSITION, AND APPLICATIONS

(71) Applicant: SHANGHAI PHARMACEUTICALS HOLDING CO., LTD., Shanghai (CN)

(72) Inventors: Jianxin Yu, Shanghai (CN); Yu Hao, Shanghai (CN); Jing Zhang, Shanghai (CN); Fei Zhao, Shanghai (CN); Leduo Zhang, Shanghai (CN); Zhenying Liu, Shanghai (CN); Gongsheng Li, Shanghai (CN); Yuji Wang, Shanghai (CN); Na Chen, Shanghai (CN); Rui Bai, Shanghai (CN); Yi Fan, Shanghai (CN)

(73) Assignee: Shanghai Phaarmaceuticals Holding Co., Ltd., Shanghai (CN)

( * ) Notice: Subject to any disclaimer, the term of this patent is extended or adjusted under 35 U.S.C. 154(b) by 0 days.

(21) Appl. No.: 16/067,144

(22) PCT Filed: Dec. 29, 2016

(86) PCT No.: PCT/CN2016/112942
§ 371 (c)(1),
(2) Date: Jun. 29, 2018

(87) PCT Pub. No.: WO2017/114452
PCT Pub. Date: Jul. 6, 2017

(65) Prior Publication Data
US 2019/0010160 A1 Jan. 10, 2019

(30) Foreign Application Priority Data

Dec. 31, 2015 (CN) .......................... 2015 1 1030013

(51) Int. Cl.
C07D 487/04 (2006.01)
A61K 31/4985 (2006.01)
C07C 59/255 (2006.01)

(52) U.S. Cl.
CPC ........ *C07D 487/04* (2013.01); *A61K 31/4985* (2013.01); *C07C 59/255* (2013.01); *C07B 2200/13* (2013.01)

(58) Field of Classification Search
CPC .................................................. C07D 487/04
USPC ....................................................... 514/249
See application file for complete search history.

(56) References Cited

FOREIGN PATENT DOCUMENTS

| CN | 104109166 A | 10/2014 |
|---|---|---|
| CN | 106928232 A | 7/2017 |
| CN | 106928233 A | 7/2017 |
| WO | 2011115069 A1 | 9/2011 |

OTHER PUBLICATIONS

International Search Report and Written Opinion for PCT/CN2016/112942, dated Apr. 11, 2017.
International Search Report issued in International Patent Application No. PCT/CN2016/112942, dated Apr. 10, 2017.
Written Opinion of the International Searching Authority issued in International Patent Application No. PCT/CN2016/112942, dated Apr. 10, 2017.
European Pharmacopoeia 6.0, "Assays," Jan. 2008, pp. 135-141, see section 2.5.12.
Priority Application—English Translation of Chinese application CN 201511030013.4, filed Dec. 31, 2015 (Not published).
First Office Action of Chinese counterpart application CN201611245708.9, dated Jun. 4, 2018.
International Search Report issued in International Patent Application No. PCT/CN2016/112943, dated Apr. 11, 2017.
Written Opinion of the International Searching Authority issued in International Patent Application No. PCT/CN2016/112943, dated Apr. 11, 2017.
Second Office Action of Chinese counterpart application CN201611245708.9, dated Nov. 21, 2018.
Notification of Reasons for Refusal issued in the counterpart Japanese patent application No. 2018-534625, dated May 7, 2019.
Takashi Kojima, "Targeting high efficiency of crystal form selection in pharmaceuticals development," Journal of Pharmaceutical Science and Technology, 2008, pp. 344-349, vol. 68, No. 5—with English translation of partial content.
"The practice of medicinal chemistry," 1999, pp. 347-365, edited by G.G. Wermuth—with English translation of partial content.
"Manual for preparation of organic compound crystals—Pharmacology and knowhow," edited by N. Hirayama, 2008 pp. 17-65—with English translation of partial content.
"Simple screening of new salt with solvent vapor," Japan Pharmaceutical Association 133th year, 2013, 29amB-150—with English translation of partial content.
Hyeseung Lee et al., "Dissolution enhancement of celecoxib via polymer-induced crystallization", Journal of Crystal Growth, Apr. 11, 2013, pp. 37-42, vol. 374.
S.L. Raghavan et al., "Crystallization of hydrocortisone acetate: influence of polymers," International Journal of Pharmaceutics, Jan. 2001, pp. 213-221, vol. 212.
Hyemin Choi et al., "Polymer-directed crystallization of atorvastatin", Journal of Pharmaceutical Sciences, Aug. 2012, pp. 2941-2951, vol. 101, No. 8.
"Manual for Solvent," edited by T. Asahara et al., 1985, pp. 47-51—with English translation of partial content.

*Primary Examiner* — Niloofar Rahmani
(74) *Attorney, Agent, or Firm* — Pilloff & Passino LLP; Sean A. Passino; Rachel K. Pilloff

(57) ABSTRACT

Disclosed is a salt of a quinoline derivative, polymorphic forms thereof, preparation methods thereof, a composition, and applications. The SPH1772 ditartrate or crystal form A thereof expresses the following excellent properties: high stability, great bioavailability, excellent pharmacokinetic properties, and better in vivo efficacy than SPH1772 free base.

9 Claims, 4 Drawing Sheets

SALT OF QUINOLONE COMPOUND, POLYMORPHS THEREOF, PREPARATION METHOD THEREFOR, COMPOSITION, AND APPLICATIONS

The present application claims the benefit of the Chinese Patent Application No. CN201511030013.4 filed on Dec. 31, 2015, the content of which is incorporated herein by reference in its entirety.

FIELD OF INVENTION

The present invention relates to a salt of quinoline derivative, and a crystal form, a preparation method, a composition and a use thereof.

PRIOR ARTS

Compound 3-(1-methyl-1H-pyrazol-4-yl)-6-(6-(1-methyl-1H-pyrazol-4-yl)-1H-[1,2,3]triazolo[4,5-b]pyrazin-1-yl)methyl)quinoline, shortened as SPH1772 (the structure is shown as below), has been disclosed in patent CN104109166A. SPH1772 is a highly potent and selective investigational oral inhibitor of hepatocyte growth factor (HGF) receptor tyrosine kinase c-Met. SPH1772 is being developed for the treatment of several solid tumors including non-small cell lung cancer (NSCLC), liver cancer, intestinal cancer and ovarian cancer, and other cancers.

Discovering materials having desirable processing properties, such as ease of handling, ease of processing, storage stability, and ease of purification, or may serve as desirable intermediate crystal forms that facilitate purification or conversion to other polymorphic forms. Polymorphs and solvates of a pharmaceutical compound or a salt thereof can also provide an opportunity to improve the performance of a pharmaceutical. It enlarges the repertoire of materials available for formulation optimization for a formulation scientist, for example by providing a product with different properties (e.g. better processing or handling characteristics, improved dissolution profile, or improved shelf-life). For at least these reasons, there is a need for a solid form of SPH1772 free base and salt thereof.

CONTENT OF THE PRESENT INVENTION

The present invention provides a salt of quinoline compound, and a crystal form, a preparation method, a composition and a use thereof. The SPH1772 ditartrate or the crystal form A thereof exhibits the following excellent properties including high stability, great bioavailability, excellent pharmacokinetic properties, and better in vivo efficacy than SPH1772 free base.

The present invention provides a quinoline compound SPH1772 ditartrate,

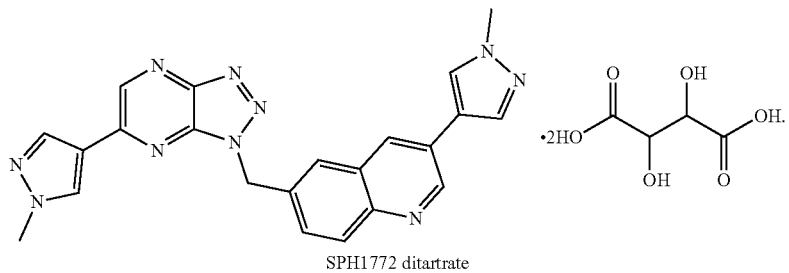

SPH1772 ditartrate

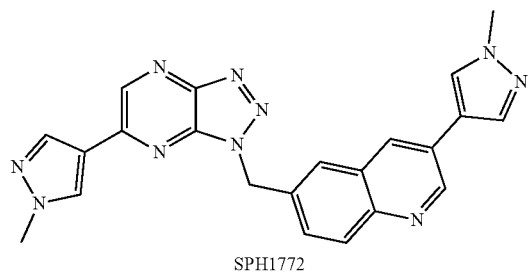 [SMILES: Cn1cc(-c2cnc3ccc(Cn4nnc5ncc(-c6cnn(C)c6)nc54)cc3c2)cn1 ; "SPH1772"]

SPH1772

Polymorphism (occurrence of different crystal forms) is a property of some molecules and molecular complexes. A single molecule may give rise to various polymorphs with different crystal structures and physical properties like melting point, thermal behavior (for example, measured by thermogravimetric analysis—"TGA", or differential scanning calorimetry (DSC)), X-ray powder diffraction (XRPD or powder XRD) pattern, infrared absorption fingerprints, and solid-state nuclear magnetic resonance (NMR) spectrum. One or more than one these techniques can be used to distinguish different polymorphs of a compound.

The tartaric acid in the quinoline compound SPH1772 ditartrate is preferably L-tartaric acid (i.e. the structure of the quinoline compound SPH1772 ditartrate is

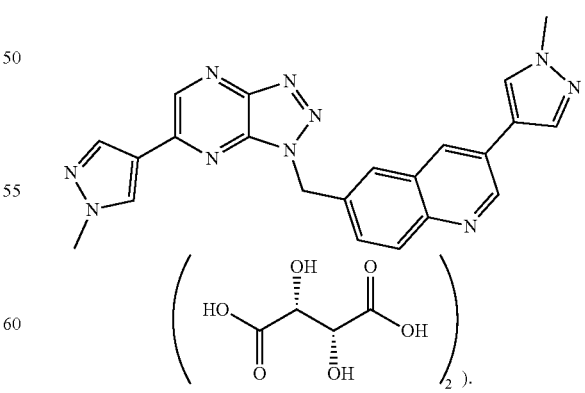

The present invention provides a crystal form A of SPH1772 ditartrate, having an X-ray powder diffraction pattern represented by diffraction angle 2θ comprising characteristic peaks at 7.5±0.2°, 9.2±0.2°, 14.5±0.2°, 16.6±0.2°, 20.3±0.2° and 28.8±0.2°; the target used in the X-ray powder diffraction is Cu target.

Preferably, the crystal form A of SPH1772 ditartrate has an X-ray powder diffraction pattern represented by diffraction angle 2θ comprising characteristic peaks at the values as shown in the left column of Table 1:

TABLE 1

XPRD peak list of crystal form A of SPH1772 ditartrate

| 2θ°[±0.2°] | Relative intensity % |
|---|---|
| 7.089 | 30.7 |
| 7.541 | 100.0 |
| 9.150 | 31.2 |
| 11.019 | 28.8 |
| 14.163 | 22.3 |
| 14.545 | 75.7 |
| 16.589 | 29.4 |
| 17.130 | 24.5 |
| 17.825 | 10.6 |
| 19.752 | 8.1 |
| 20.283 | 32.9 |
| 21.389 | 24.9 |
| 21.598 | 21.7 |
| 22.783 | 12.8 |
| 23.161 | 6.3 |
| 25.314 | 29.5 |
| 25.789 | 22.3 |
| 26.670 | 8.5 |
| 26.927 | 8.9 |
| 28.264 | 6.3 |
| 28.758 | 25.1 |
| 29.348 | 10.5 |
| 31.248 | 3.4 |
| 32.305 | 6.5 |
| 33.048 | 3.1 |
| 33.842 | 4.6 |
| 35.343 | 3.5 |
| 38.305 | 4.4 |

Preferably, the crystal form A of SPH1772 ditartrate has an X-ray powder diffraction pattern represented by diffraction angle 2θ comprising characteristic peaks and relative intensity at the values as shown in Table 1.

Preferably, the crystal form A of SPH1772 ditartrate has an X-ray powder diffraction pattern represented by diffraction angle 2θ as shown in FIG. 1.

Preferably, the melting point of the crystal form A of SPH1772 ditartrate is 202° C.

Preferably, DSC of crystal form A of SPH1772 ditartrate has a main endothermic peak at 199.4° C. (DSC is differential scanning calorimetry).

The crystal form A of SPH1772 ditartrate can be prepared according to the content disclosed in the embodiments of the present application and common knowledge in the art.

The present invention also provides a preparation method for the crystal form A of SPH1772 ditartrate comprising in an organic solvent, reacting the compound SPH1772 with tartaric acid; wherein the organic solvent is an alcoholic solvent, an ester solvent, a mixed solvent of DCM:MeOH=6:1 to 9:1 v/v, an ether solvent or a ketone solvent.

In the preparation method for the crystal form A of SPH1772 ditartrate, the alcoholic solvent is preferably methanol; the ester solvent is preferably ethyl acetate; the ether solvent is preferably tetrahydrofuran; the ketone solvent is preferably acetone. The volume/mass ratio of the organic solvent to the SPH1772 is preferably 40 mL/g to 80 mL/g, more preferably 60 to 70 mL/g. The molar ratio of SPH1772 to the tartaric acid is preferably 1:2.0 to 1:2.2, more preferably 1:2.1; the reaction temperature is preferably 40 to 60° C., more preferably 50° C.; the reaction time is preferably 24 h to 72 h, more preferably 24 h to 48 h.

The preparation method for the crystal form A of SPH1772 ditartrate, preferably comprises adding the tartaric acid to "mixture of the compound SPH1772 and the organic solvent". The tartaric acid is preferably added over 1 to 5 minutes, more preferably 2 minutes; the tartaric acid can also participate in the reaction in the form of a "solution of tartaric acid in the organic solvent", in the "solution of tartaric acid in the organic solvent", the volume/molar ratio of the organic solvent to the tartaric acid is preferably 3.5:1 to 4.5:1 mL/mmol, more preferably 4:1 mL/mmol. When the tartaric acid participates in the reaction in the form of a "solution of tartaric acid in the organic solvent", the addition rate of the "solution of tartaric acid in the organic solvent" is preferably 1 to 5 mL/min, more preferably 2.5 mL/min. The compound SPH1772 and the organic solvent are preferably mixed by adding the compound SPH1772 to the organic solvent to give the "mixture of the compound SPH1772 and the organic solvent".

The preparation method for the crystal form A of SPH1772 ditartrate, after the reaction is complete, can further comprise post-treatment which includes filtering the reaction solution to give the crystal form A of SPH1772 ditartrate. After the filtration, an operation of washing the filter cake with the organic solvent can be further comprised. After the filtration, an operation of drying the filter cake can be further comprised; the drying is preferably under vacuum; the drying under vacuum is preferably at 40 to 60° C., more preferably 50° C.

The present invention also provides a preparation method for a crystal form B of SPH1772 ditartrate, which is any of the following methods:

method 1: the crystal form A of SPH1772 ditartrate is subjected to a gas-liquid infiltration crystallization experiment; wherein the good solvent is THF:H₂O=19:1 v/v; the anti-solvent is butanone (MEK);

method 2: a solution of the crystal form A of SPH1772 ditartrate in 1,4-dioxane is subjected to a room-temperature solvent evaporation crystallization experiment;

method 3: the crystal form A of SPH1772 ditartrate is subjected to a superpolymer-induced crystallization experiment; wherein when the mass ratio of polyvinylpyrrolidone (PVP):polyvinyl alcohol (PVA):polyvinyl chloride (PVC):polyvinyl acetate (PVAC):hydroxypropyl methyl cellulose (HPMC):methyl cellulose (MC) as superpolymer is 1:1:1:1:1:1, the solvent is 1,4-dioxane; when the mass ratio of polycaprolactone (PCL):polyethylene glycol (PEG):polymethyl methacrylate (PMMA):sodium alginate (SA):hydroxyethyl cellulose (HEC) as superpolymer is 1:1:1:1:1, the solvent is 1,4-dioxane, or tetrahydrofuran:water=19:1 v/v.

In the present invention, the gas-liquid infiltration crystallization experiment is a conventional method for preparing a crystal form in the art, and the specific operation comprises that placing a small vessel containing a "saturated solution of a compound in a good solvent" open-mouthed in a large vessel containing an anti-solvent, the large vessel is sealed and allows to stand, when solid precipitates out, the solid is collected; wherein the small vessel cannot be submerged in the anti-solvent contained in the vessel.

In the present invention, the method 1 of the preparation method for the crystal form B of SPH1772 ditartrate preferably comprises that a saturated solution of the crystal form A of SPH1772 ditartrate in the good solvent can be prepared by mixing the crystal form A of SPH1772 ditartrate with the good solvent and taking the supernatant; wherein the mass/ volume ratio of the crystal form A of SPH1772 ditartrate to the good solvent is preferably 4 to 6 mg/mL.

In the present invention, the room-temperature solvent evaporation crystallization experiment is a conventional method for preparing a crystal form in the art, and the specific operation comprises that sealing a vessel containing a "clear solution of a compound in a solvent" with a sealing membrane and placing at room temperature, after the sealing membrane is punctured a few holes (e.g. 2 to 4 holes), the solvent naturally evaporates to dry to give solid.

In the present invention, in the method 2 of the preparation method for the crystal form B of SPH1772 ditartrate, the solution of the crystal form A of SPH1772 ditartrate in 1,4-dioxane can comprise mixing the crystal form A of SPH1772 ditartrate with 1,4-dioxane, then taking the supernatant liquid; the mass/volume ratio of the crystal form A of SPH1772 ditartrate to 1,4-dioxane is preferably 5 to 10 mg/mL.

In the present invention, the superpolymer-induced crystallization experiment is a conventional method for preparing a crystal form in the art, and the specific operation comprises that after a saturated solution of a compound in a solvent is sufficiently mixed with a superpolymer (usually ultrasound is used to make it sufficiently mixed), the vessel is covered with a punctured sealing membrane, the solvent evaporates at room temperature, the solid is collected.

In the present invention, in the method 3 of the preparation method for the crystal form B of SPH1772 ditartrate, the volume/mass of the saturated solution of the crystal form A of SPH1772 ditartrate to the superpolymer is preferably 0.75:1 to 1.5:1.

The present invention also provides a crystal form B of SPH1772 ditartrate prepared by the preparation method for the crystal form B of SPH1772 ditartrate mentioned above.

The present invention also provides a preparation method for a crystal form C of SPH1772 ditartrate, comprising that the crystal form A of SPH1772 ditartrate is subjected to a gas-solid infiltration crystallization experiment; wherein the solvent is N,N-dimethylformamide.

In the present invention, gas-solid infiltration crystallization experiment is a conventional method for preparing a crystal form in the art, and the specific operation comprises that open-mouthed placing a small vessel containing a compound in a large vessel containing a solvent, the large vessel is sealed and allows to stand, when solid precipitates out, the solid is collected.

In the present invention, in the preparation method for the crystal form C of SPH1772 ditartrate, the mass/volume ratio of the crystal form A of SPH1772 ditartrate to the solvent is preferably 4 to 7 mg/mL, more preferably 5 mg/mL.

The present invention also provides a crystal form C of SPH1772 ditartrate prepared by the preparation method for the crystal form C of SPH1772 ditartrate mentioned above.

The present invention also provides a preparation method for a crystal form D of SPH1772 ditartrate, comprising that the crystal form A of SPH1772 ditartrate is subjected to a gas-solid infiltration crystallization experiment; wherein the solvent is DMSO.

In the present invention, in the preparation method for the crystal form D of SPH1772 ditartrate, the mass/volume ratio of the crystal form A of SPH1772 ditartrate to the solvent is preferably 4 to 7 mg/mL, more preferably 5 mg/mL.

The present invention also provides a crystal form D of SPH1772 ditartrate prepared by the preparation method for the crystal form D of SPH1772 ditartrate mentioned above.

The present invention also provides a use of SPH1772 ditartrate in preparing a tyrosine kinase c-Met inhibitor.

The present invention also provides a use of SPH1772 ditartrate in preparing a medicament for the treatment and/or prophylaxis of a disease associated with overexpression or activity of tyrosine kinase c-Met.

The present invention also provides a use of the crystal form A of SPH1772 ditartrate in preparing a tyrosine kinase c-Met inhibitor.

The present invention also provides a use of the crystal form A of SPH1772 ditartrate in preparing a medicament for the treatment and/or prophylaxis of a disease associated with overexpression or activity of tyrosine kinase c-Met.

The present invention also provides a composition, comprising an effective dose of SPH1772 ditartrate, and a pharmaceutically acceptable excipient.

The present invention also provides a composition, comprising an effective dose of the crystal form A of SPH1772 ditartrate, and a pharmaceutically acceptable excipient.

The present invention also provides a use of the crystal form of SPH1772 ditartrate selected from the group consisting of the crystal form B of SPH1772 ditartrate, crystal form C of SPH1772 ditartrate and crystal form D of SPH1772 ditartrate in preparing a tyrosine kinase c-Met inhibitor.

The present invention also provides a use of the crystal form of SPH1772 ditartrate selected from the group consisting of crystal form B of SPH1772 ditartrate, crystal form C of SPH1772 ditartrate and crystal form D of SPH1772 ditartrate in preparing a medicament for the treatment and/or prophylaxis of a disease associated with overexpression or activity of tyrosine kinase c-Met.

The present invention also provides a composition, comprising the crystal form of SPH1772 ditartrate selected from the group consisting of crystal form B of SPH1772 ditartrate, crystal form C of SPH1772 ditartrate and crystal form D of SPH1772 ditartrate, and a pharmaceutically acceptable excipient.

In the present invention, the pharmaceutically acceptable excipient is conventionally pharmaceutical excipient in the art, the select of the pharmaceutically acceptable excipient varies depending on the route of administration and the characteristic of action, preferably includes fillers, diluents, adhesives, wetting agents, disintegrants, lubricants, emulsifiers, and suspending agents.

In the present invention, the route of administration of the pharmaceutical composition can be oral administration, injection (intravenous, intramuscular, subcutaneous and intracoronary), sublingual administration, buccal administration, rectal administration, transurethral administration, transvaginal administration, nasal administration, inhaled administration or topical administration, preferably oral administration.

In the present invention, the disease associated with overexpression or activity of tyrosine kinase c-Met is a conventional disease caused by the change of tyrosine kinase c-Met in the art, preferably includes cancer, musculoskeletal sarcoma, soft tissue sarcoma, hematopoietic malignancy and other tumors. The cancer preferably includes bladder cancer, breast cancer, cervical cancer, colon cancer, esophageal cancer, stomach cancer, head and neck cancer, kidney cancer, lung cancer, liver cancer, nasopharyngeal cancer, ovarian cancer, pancreatic cancer, prostate cancer and thyroid cancer; the musculoskeletal sarcoma preferably includes osteosarcoma, synovial sarcoma and rhabdomyosarcoma; the soft tissue sarcoma preferably includes malignant fibrous histocytoma/fibrosarcoma, leiomyosarcoma and Kaposi's sarcoma; the hematopoietic malignancy preferably includes multiple myeloma, lymphoma, adult T-cell leukemia, acute myeloid leukemia and chronic myelogenous leukemia; the other tumors preferably include glioblastoma tumor, astrocytoma, melanoma, mesothelioma and embryonal carcinosarcoma.

Unless otherwise specified, the tartaric acid in the present invention generally refers to L-tartaric acid. For example, the tartaric acid contained in the SPH1772 ditartrate and the crystal form A to D thereof generally refers to L-tartaric acid. The structure of L-tartaric acid is

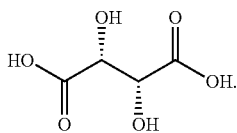

In the present application, the salt of the quinoline compound SPH1772 or the polymorph thereof (the SPH1772 ditartrate or the crystal form A thereof) is generally characterized by graphical data "as shown in the figure". These data include (e.g.) powder X-ray diffraction pattern, FTIR spectrum, and solid-state NMR spectrum. A skilled person will understand that these representations of the data may be subject to small changes such as peak relative intensity and peak position due to factors such as changes of instrument response and changes of sample concentration and purity which are well known to the skilled person. Nonetheless, the skilled person will be readily able to compare the graphical data in the figures herein with the graphical data generated from an unknown crystal form and confirm whether the two sets of graphical data characterize the same crystal form or two different crystal forms. The SPH1772 ditartrate or the crystal form A thereof is herein referred to as being characterized by graphical data "as shown in the figure", and therefore it will be understood that it can include any crystal forms of SPH1772 ditartrate or crystal form A thereof characterized by graphical data with such minor changes (as known to the skilled person) as compared to the figures herein.

The terms XRPD and PXRD are used interchangeably in the scientific literature by those skilled in the art of powder X-ray diffraction analysis, and the present application makes no distinction between these two expressions or their abbreviations.

As used herein, unless otherwise specified, XRPD is performed by using a Cu Ka radiation of wavelength $\lambda$=1.5406 Å.

Articles (e.g. reaction mixture) may be characterized herein as being, or allowed to reach "room temperature", often abbreviated as "RT". This means that the temperature of the article is close to the temperature of the space, or the same as the temperature of the space, example of the space can be the room or fume cupboard where the article is located. Typically, the room temperature is about 20° C. to about 30° C., or about 22° C. to about 27° C., or about 25° C.

The method or step herein may be referred to as "overnight". This refers to, for example, the time interval of a method or step spans the night time when the method or step may not be actively observed. The time interval is about 8 to about 20 hours, or about 10 to 18 hours, typically about 16 hours.

As used herein, the term "reduced pressure" refers to a pressure of about 10 mbar to about 50 mbar.

As used herein, the term "isolated" refers to any of the following cases: the salt of SPH1772 or the polymorph thereof in the present invention, and corresponding to SPH1772 or the polymorph of the salt of SPH1772 physically separated from the reaction mixture formed therefrom.

The present invention relates to an active pharmaceutical ingredient API (e.g. SPH1772 ditartrate or the crystal form A thereof) containing an individual optical isomer of SPH1772, a mixture of individual enantiomers or a racemate.

The SPH1772 ditartrate or the crystal form A thereof in the present invention generally exhibits reduced hygroscopicity. Because these salts do not have a water absorption as strong as comparative salts in the art, they have advantages in a galenic formulation.

Preferably, the crystal form A of SPH1772 ditartrate in the present invention is at least in the form of partially crystal, a higher degree of crystallinity results in a more stable salt of SPH1772.

Preferably, the SPH1772 ditartrate in the present invention has a water content of less than 0.1% to 8% by weight, more preferably 0.5% to 5% by weight, more preferably 0.8% to 3.5% by weight.

The SPH1772 ditartrate or the crystal form A thereof in the present invention preferably exists in an isolated and a substantially pure form such as >95% by weight, preferably >98% by weight, more preferably >99% by weight.

The SPH1772 ditartrate or the crystal form A thereof in the present invention preferably exists in the form of microparticle.

Without violating the common sense in the art, the above preferred conditions can be arbitrarily combined, then preferred embodiments of the present invention are obtained.

The reagents and raw materials used in the present invention are commercially available.

The positive and progressive effect of the present invention is that the SPH1772 ditartrate or the crystal form A thereof expresses the following excellent properties which include high stability, great bioavailability, excellent pharmacokinetic properties, and better in vivo efficacy than SPH1772 free base.

DETAILED DESCRIPTION OF THE PREFERRED EMBODIMENT

The following embodiments further illustrate the present invention, but the present invention is not limited thereto.

The experimental methods that do not specify the specific conditions in the following embodiments are selected according to conventional methods and conditions, or according to the description of the product.

In the embodiments of the present invention, unit M refers to mol/L, nM refers to nmol/L, mM refers to mmol/L.

Unless otherwise specified, the tartaric acid in the following embodiments is L-tartaric acid.

Unless otherwise specified, the devices and test methods involved in the embodiments of the present invention were as follows:

XRPD pattern: samples were analyzed on a PANalytical Empyrean powder X-ray diffractometer; the measurement conditions were as follows:

| Parameter | XRPD |
|---|---|
| X-ray | Cu, kα, Kα1 (Å): 1.540598; Kα2 (Å): 1.544426 |
| X-ray tube settings | Kα2/Kα1 strength ratio: 0.50 |
| Divergence slit | 45 kV, 40 mA |
| Monochromator | automatic |
| Scan mode | none |
| Scan range (°2Theta) | continuous |
| Scan step size (°2Theta) | 3°~40° |
| Scan time (minute) | 0.013 |

Residual moisture content: determined according to the Karl Fischer method as described in *Ph. Eur.* 6th edition, 2008, section 2.5.12. Measurements were performed using a Mettler Toledo DL31 Karl Fischer titrator. Typically, 50 mg to 100 mg salt samples were analyzed.

IR: Perkin Elmer type of diffuse reflection mode;
DSC: TA Q200/2000 differential scanning calorimeter;
TGA: TA Q500/5000 thermogravimetric analyzer;

| Parameter | TGA | DSC |
|---|---|---|
| Method | linear warming | linear warming |
| Sample tray | platinum plate, open | aluminum plate, gland |
| temperature range | room temperature-set temperature | 25° C.-set temperature |
| Scan rate (° C./minute) | 10 | 10 |
| Protective gas | nitrogen | nitrogen |

Melting point: Lab India Visual melting range apparatus;
HPLC: high performance liquid chromatography;
High performance liquid chromatography was performed on Agilent 1100 and 1260 HPLC.

| Parameter | Purity |
|---|---|
| chromatographic column | Agilent C18 (4.6 × 150 mm 3.5 μm) |
| Mobile phase | A: 0.1% trifluoroacetic acid aqueous solution B: 0.1% trifluoroacetic acid in acetonitrile |

| | Time (minute) | % B |
|---|---|---|
| Gradient | 0.0 | 10 |
| | 10.0 | 30 |
| | 20.0 | 90 |
| | 22.0 | 90 |
| | 22.1 | 10 |
| | 25.0 | 10 |

| | |
|---|---|
| Time | 25.0 minute |
| Post-running time | 0.0 minute |
| Flow rate | 1.0 mL/min |
| injection volume | 5 μL |
| Detection wavelength | 250 nm (blank: 500 nm) |
| Column temperature | 30° C. |
| Sample chamber temperature | room temperature |
| Diluent | 50 μL + acetonitrile |

Solution NMR: solution nuclear magnetic resonance spectrum was determined on Bruker 400M NMR spectrometer with DMSO-$d_6$ as a solvent.

Embodiment 1: Crystal Form A of SPH1772

Figure 2:
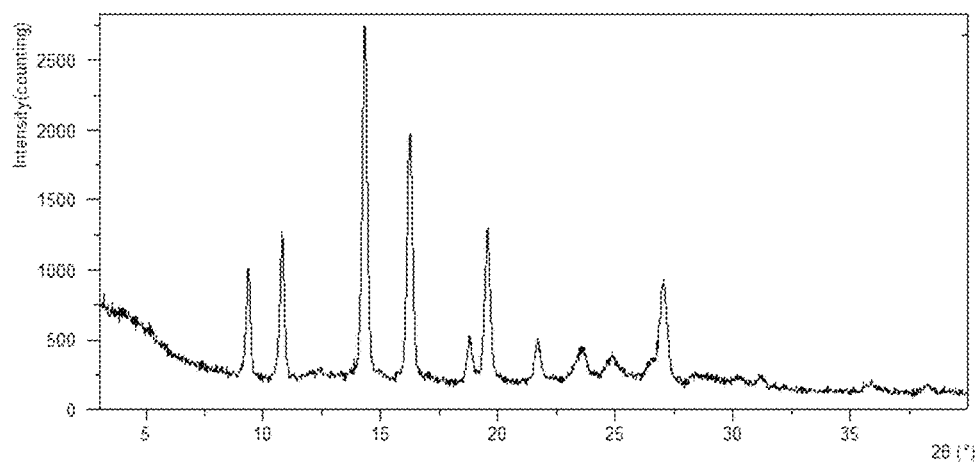
FIG. 2 is XRPD pattern of crystal form A of SPH1772.

A mixture of 5.0 g (11.8 mmol) SPH 1772 and 100 mL DMF was loaded to a three-necked round-bottomed flask equipped with a magnetic needle, thermometer, and nitrogen balloon, heated to 110° C., slowly dissolved to a clear solution, stirred at this temperature for 30 minutes, stopped heating and allowed to stand overnight at room temperature. The mixture was filtered and the filter cake was washed with 20 mL DMF. The above filter cake was transferred to a three-neck round-bottomed flask equipped with a magnetic needle, thermometer and nitrogen balloon, and 100 mL anhydrous ethanol was added. The mixture was heated to 50° C., and stirred at this temperature for 2 hours, stopped heating, cooled to room temperature. The mixture was filtered and the filter cake was washed with 20 mL anhydrous ethanol. The solid was placed in a vacuum oven at 50° C. for 2 hours to give 4.0 g (80%) white product. The XPRD peak list of crystal form A of SPH1772 is shown below; the XRPD pattern is shown in FIG. 2.

| 2θ[±0.2°] | Relative intensity % |
|---|---|
| 9.374 | 31.0 |
| 10.811 | 42.6 |
| 12.219 | 1.6 |
| 14.321 | 100.0 |
| 16.239 | 72.2 |
| 18.813 | 11.3 |
| 19.546 | 44.8 |
| 21.682 | 12.3 |
| 23.673 | 9.5 |
| 24.813 | 7.0 |
| 27.005 | 29.4 |
| 28.567 | 1.6 |
| 35.797 | 1.9 |
| 38.200 | 1.9 |

DSC showed a main endothermic peak at 273.0° C.

IR (cm$^{-1}$): 3432.3, 1618.2, 1575.9, 1541.7, 1195.9, 1126.6, 1099.6, 917.8, 817.7 and 616.9.

Residual solvent—not detected.

Melting point=270.5° C.

$^1$H NMR (δppm, DMSO-$d_6$, 400 MHz) 9.22 (s, 1H), 9.17 (d, J=2.4 Hz, 1H), 8.64 (s, 1H), 8.46 (d, J=1.6 Hz, 1H), 8.37 (s, 1H), 8.31 (s, 1H), 8.07 (s, 1H), 7.99 (d, J=8.8 Hz, 1H), 7.84 (d, J=1.2 Hz, 1H), 7.76 (dd, $J_1$=8.4 Hz, $J_2$=2.0 Hz, 1H), 6.15 (s, 2H), 3.95 (s, 3H), 3.90 (s, 3H).

Embodiment 2: Preparation of Crystal Form A of SPH1772 Ditartrate

Ethyl acetate (10 mL) was added to SPH1772 free base (250.8 mg, 0.59 mmol), the mixture was stirred at room temperature to give a white suspension, a solution of tartaric acid (187.5 mg, 1.25 mmol) in ethyl acetate (5 mL) was added over two minutes. The mixture was stirred at 50° C. for 24 hours, then filtered and the filter cake was rinsed with MeOH (5 mL), the solid was transferred to a 50° C. vacuum oven and dried overnight to give 370.5 mg (yield 86.3%) white solid.

DSC showed a main endothermic peak at 199.4° C.

Figure 1:
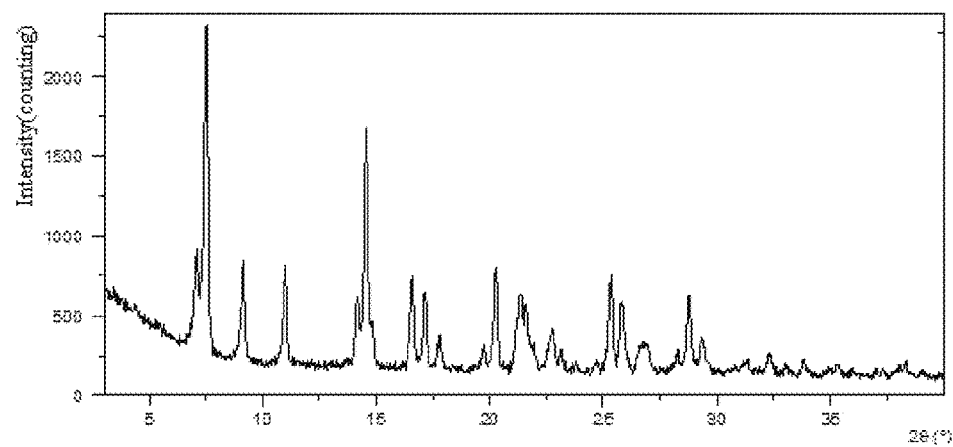
FIG. 1 is XRPD pattern of crystal form A of SPH1772 ditartrate.

The XRPD pattern is shown in FIG. 1, the XPRD peak list is shown below:

| 2θ°[±0.2°] | Relative intensity % |
|---|---|
| 7.089 | 30.7 |
| 7.541 | 100.0 |
| 9.150 | 31.2 |
| 11.019 | 28.8 |
| 14.163 | 22.3 |
| 14.545 | 75.7 |
| 16.589 | 29.4 |
| 17.130 | 24.5 |
| 17.825 | 10.6 |
| 19.752 | 8.1 |
| 20.283 | 32.9 |
| 21.389 | 24.9 |
| 21.598 | 21.7 |
| 22.783 | 12.8 |
| 23.161 | 6.3 |
| 25.314 | 29.5 |
| 25.789 | 22.3 |
| 26.670 | 8.5 |
| 26.927 | 8.9 |
| 28.264 | 6.3 |
| 28.758 | 25.1 |
| 29.348 | 10.5 |
| 31.248 | 3.4 |
| 32.305 | 6.5 |
| 33.048 | 3.1 |
| 33.842 | 4.6 |
| 35.343 | 3.5 |
| 38.305 | 4.4 |

IR (cm$^{-1}$): 3415.3, 3225.4, 3117.1, 2356.6, 1742.6, 1714.0, 1579.5, 1541.8, 1191.2, 1135.7, 1076.4, 873.7 and 608.2.

Residual solvent—not detected.

Melting point=202° C.

$^1$HNMR indicated the existence of tartrate.

$^1$HNMR (δppm, DMSO-d$_6$, 400 MHz) 9.22 (s, 1H), 9.18 (d, J=0.4 Hz, 1H), 8.64 (s, 1H), 8.46 (d, J=0.4 Hz, 1H), 8.37 (s, 1H), 8.31 (s, 1H), 8.07 (s, 1H), 7.99 (d, J=0.8 Hz, 1H), 7.84 (d, J=1.2 Hz, 1H), 7.76 (dd, J$_1$=8.4 Hz, J$_2$=2.0 Hz, 1H), 6.16 (s, 2H), 4.33 (s, 4H), 3.95 (s, 3H), 3.90 (s, 3H).

Embodiment 3: Polymorphism Study of SPH1772 Tartrate

The crystal form A of SPH1772 ditartrate used in this embodiment was all prepared from Embodiment 2.

The polymorphism study was performed under 96 kinds of conditions including antisolvent addition, room temperature stirring, gas-solid infiltration, gas-liquid infiltration, slowly cooling, room-temperature solvent evaporation and superpolymer-induced crystallization etc. The solid obtained in the test has been completely separated and characterized.

(1) Antisolvent Addition 15 mg crystal form A of SPH1772 ditartrate was added to a 20 mL vial, an appropriate good solvent was added to dissolve the solid, an anti-solvent was added dropwise under stirring. After solid was precipitated out, the solid was separated by centrifugation. If 15 mL anti-solvent was added and no solid was precipitated out after stirring overnight, the solution was allowed to evaporate at room temperature and the solid was isolated therefrom. The result is shown in Table 2.

TABLE 2 added anti-solvent and the crystal form

| Test number | Good solvent/ Anti-solvent | Good solvent (mL)/ Anti-solvent (mL) | crystal form |
|---|---|---|---|
| SPH-A-1 | THF/n-heptane | 3.4/4.8 | amorphous |
| SPH-A-2 | THF/toluene | 3.4/12.0 | amorphous |
| SPH-A-3* | THF/EtOAc | 3.4/12.0 | amorphous |
| SPH-A-4* | THF/MEK | 3.4/12.0 | amorphous |
| SPH-A-5 | 1,4-dioxane/CHCl$_3$ | 2.6/12.0 | amorphous |
| SPH-A-6* | 1,4-dioxane/ACN | 2.6/12.0 | amorphous |
| SPH-A-7 | 1,4-dioxane/IPA | 2.6/12.0 | amorphous |
| SPH-A-8 | (acetone:H$_2$O)/n-heptane | 5.0/5.0 | amorphous |
| SPH-A-9 | (acetone:H$_2$O)/EtOAc | 5.0/10.0 | crystal form A of SPH1772 monotartrate |
| SPH-A-10 | NMP/toluene | 0.6/12.0 | amorphous |
| SPH-A-11** | NMP/EtOAc | 0.6/15.0 | amorphous |
| SPH-A-12* | NMP/MEK | 0.6/15.0 | crystal form A of SPH1772 |
| SPH-A-13 | DMAc/CHCl$_3$ | 2.0/12.0 | amorphous |
| SPH-A-14 | DMAc/MTBE | 2.0/15.0 | crystal form B of SPH1772 |
| SPH-A-15* | DMAc/IPAc | 2.0/15.0 | crystal form A of SPH1772 |
| SPH-A-16* | DMSO/ACN | 3.0/12.0 | amorphous |
| SPH-A-17** | DMSO/MIBK | 3.0/12.0 | amorphous |
| SPH-A-18* | DMSO/EtOH | 3.0/12.0 | amorphous |

Note:
In the table, acetone:H$_2$O = 4:1, v/v;
*indicates that the solid is obtained by stirring overnight at 5° C.;
**indicates that the solid is obtained by solvent evaporating at room temperature.

The anti-solvent addition method was performed under 18 kinds of experimental conditions, thereby obtaining crystal forms including crystal form A of SPH1772 monotartrate, crystal form A of SPH1772, and crystal form B of SPH1772.

(2) Gas-Solid Infiltration Method 10 mg crystal form A of SPH1772 ditartrate was added to a 3 mL vial, 2 mL solvent was added to a 20 mL vial, the 3 mL vial was open-mouthed placed in the 20 mL vial, and the 20 mL vial was sealed. The solid was collected after the vial stood at room temperature for 7 days. The result is shown in Table 3.

TABLE 3 the solvent used in gas-solid infiltration experiment and the crystal form obtained

| Test number | Solvent | crystal form |
|---|---|---|
| SPH-B-A1 | H$_2$O | crystal form A of SPH1772 ditartrate |
| SPH-B-A2 | DCM | crystal form A of SPH1772 ditartrate |
| SPH-B-A3 | EtOH | crystal form A of SPH1772 ditartrate |
| SPH-B-A4 | MeOH | crystal form A of SPH1772 ditartrate |
| SPH-B-A5 | ACN | crystal form A of SPH1772 ditartrate |
| SPH-B-A6 | THF | crystal form A of SPH1772 ditartrate |
| SPH-B-A7 | CHCl$_3$ | crystal form A of SPH1772 ditartrate |
| SPH-B-A8 | MEK | crystal form A of SPH1772 ditartrate |
| SPH-B-A9 | Acetone | crystal form A of SPH1772 ditartrate |
| SPH-B-A10 | DMF | crystal form C of SPH1772 ditartrate |

TABLE 3-continued the solvent used in gas-solid infiltration experiment and the crystal form obtained

| Test number | Solvent | crystal form |
| --- | --- | --- |
| SPH-B-A11 | EtOAc | crystal form A of SPH1772 ditartrate |
| SPH-B-A12 | 1,4-Dioxane | crystal form A of SPH1772 ditartrate |
| SPH-B-A13 | IPA | crystal form A of SPH1772 ditartrate |
| SPH-B-A14 | DMSO | crystal form D of SPH1772 ditartrate |

The gas-solid infiltration method was performed under 14 kinds of experimental conditions, thereby obtaining crystal forms including crystal form A of SPH1772 ditartrate, crystal form C of SPH1772 ditartrate, and crystal form D of SPH1772 ditartrate.

(3) Room Temperature Stirring Method:

15 mg crystal form A of SPH1772 ditartrate was added to a 1.5 mL vial, 1.0 mL various solvent or mixed solvent was added to form a suspension, which was subjected to magnetic stirring with a set temperature of 25° C. (800 rpm), after about 3.5 days, the solid was separated by centrifugation, and the solution that became clear after stirring evaporated at room temperature and solid was separated. The result is shown in Table 4.

TABLE 4 the solvent used in the room temperature stirring experiment and the crystal form obtained

| Test number | Solvent | crystal form |
| --- | --- | --- |
| SPH-C-A1 | EtOH | crystal form A of SPH1772 ditartrate |
| SPH-C-A2 | IPA | crystal form A of SPH1772 ditartrate |
| SPH-C-A3 | acetone | crystal form A of SPH1772 ditartrate |
| SPH-C-A4 | MIBK | crystal form A of SPH1772 ditartrate |
| SPH-C-A5 | EtOAc | crystal form A of SPH1772 ditartrate |
| SPH-C-A6 | IPAc | crystal form A of SPH1772 ditartrate |
| SPH-C-A7 | MTBE | crystal form A of SPH1772 ditartrate |
| SPH-C-A8 | THF | crystal form A of SPH1772 ditartrate |
| SPH-C-A9 | 2-MeTHF | crystal form A of SPH1772 ditartrate |
| SPH-C-A10 | 1,4-dioxane | crystal form A of SPH1772 ditartrate |
| SPH-C-A11 | ACN | crystal form A of SPH1772 ditartrate |
| SPH-C-A12 | DCM | crystal form A of SPH1772 ditartrate |
| SPH-C-A13 | MEK | crystal form A of SPH1772 ditartrate |
| SPH-C-A14 | MeOH | amorphous |
| SPH-C-A15 | MeOH/H$_2$O (aw = 0.2) | crystal form A of SPH1772 ditartrate |
| SPH-C-A16 | MeOH/H$_2$O (aw = 0.4) | amorphous |
| SPH-C-A17 | MeOH/H$_2$O (aw = 0.6) | amorphous |
| SPH-C-A18 | MeOH/H$_2$O (aw = 0.8) | amorphous |
| SPH-C-A19 | H$_2$O | amorphous |

Wherein, aw refers to water activity.

The room temperature stirring method was performed under 19 kinds of experimental conditions, thereby obtaining crystal form A of SPH1772 ditartrate.

(4) 50° C. Stirring Method:

15 mg crystal form A of SPH1772 ditartrate was added to a 1.5 mL glass vial, 0.5 mL solvent listed in Table 5 was respectively added to form a suspension, which was stirred at 50° C. for 3.5 days, then the solid was collected by centrifugation and subjected to XRPD measurement. The result is shown in Table 5.

TABLE 5 the solvent used in the 50° C. stirring experiment and the crystal form obtained

| Test number | Solvent | Crystal form |
| --- | --- | --- |
| SPH-D-A1 | EtOH | crystal form A of SPH1772 ditartrate |
| SPH-D-A2 | IPA | crystal form A of SPH1772 ditartrate |
| SPH-D-A3 | acetone | crystal form A of SPH1772 ditartrate |
| SPH-D-A4 | MIBK | crystal form A of SPH1772 ditartrate |
| SPH-D-A5 | EtOAc | crystal form A of SPH1772 ditartrate |
| SPH-D-A6 | IPAc | crystal form A of SPH1772 ditartrate |
| SPH-D-A7 | MTBE | crystal form A of SPH1772 ditartrate |
| SPH-D-A8 | THF | crystal form A of SPH1772 ditartrate |
| SPH-D-A9 | 2-MeTHF | crystal form A of SPH1772 ditartrate |
| SPH-D-A10 | 1,4-dioxane | crystal form A of SPH1772 ditartrate |
| SPH-D-A11 | ACN | crystal form A of SPH1772 ditartrate |
| SPH-D-A12 | CHCl$_3$ | crystal form A of SPH1772 ditartrate |
| SPH-D-A13 | MEK | crystal form A of SPH1772 ditartrate |
| SPH-D-A14 | MeOH | amorphous |

The 50° C. stirring experiment was performed under 14 kinds of experimental conditions, thereby obtaining crystal form A of SPH1772 ditartrate.

(5) Slowly Cooling Experiment 30 mg crystal form A of SPH1772 ditartrate was added to a 3 mL vial, 1.0 mL various solvent was added, the mixture was stirred at 50° C. for about 2 hours and filtered to give a saturated solution thereof, the solution was cooled to 5° C. at a rate of 0.1° C./min, and then solid was precipitated out. The sample failing to precipitate solid was evaporated at room temperature and solid was separated. The result is shown in Table 6.

TABLE 6 the solvent used in the slowly cooling experiment and the crystal form obtained

| Test number | Solvent (v:v) | Crystal form |
| --- | --- | --- |
| SPH-E-A1* | 1,4-dioxane | amorphous |
| SPH-E-A2 | 2-MeTHF | amorphous |
| SPH-E-A3* | acetone | amorphous |
| SPH-E-A4* | EtOAc | amorphous |
| SPH-E-A5* | ACN | amorphous |
| SPH-E-A6 | THF/H$_2$O (19:1) | amorphous |

Note:
*refers to that the solid was obtained by solvent evaporating at room temperature.

The slowly cooling experiment was performed under 6 kinds of experimental conditions, thereby obtaining amorphous solid of SPH1772 tartrate.

(5) Gas-Liquid Infiltration Experiment:

15 mg crystal form A of SPH1772 ditartrate was added to a 3 mL vial, 2.5 mL solvent listed in Table 7 was added respectively, filtered, the supernatant was placed in a 3 mL vial, another 20 mL vial was used to which approximately 3 mL anti-solvent was added, the 3 mL vial was open-mouthed placed in a 20 mL vial, the 20 mL vial was then sealed and allowed to stand at room temperature. When precipitate was observed, the precipitate was measured by XRPD. The result is shown in Table 7.

TABLE 7 the solvent in the gas-liquid infiltration experiment and the crystal form obtained

| Test number | Good solvent/Anti-solvent | Crystal form |
|---|---|---|
| SPH-F-A1 | (THF:H₂O)/MEK | crystal form B of SPH1772 ditartrate |
| SPH-F-A2 | (THF:H₂O)/ACN | amorphous |
| SPH-F-A3 | (THF:H₂O)/EtOH | amorphous |
| SPH-F-A4 | 1,4-dioxane/MEK | clear |
| SPH-F-A5 | 1,4-dioxane/n-heptane | amorphous |
| SPH-F-A6 | 1,4-dioxane/EtOAc | amorphous |
| SPH-F-A7 | NMP/MeOH | crystal form A of SPH1772 |
| SPH-F-A8 | NMP/toluene | clear |
| SPH-F-A9 | NMP/ACN | crystal form A of SPH1772 |
| SPH-F-A10 | DMSO/acetone | clear |
| SPH-F-A11 | DMSO/IPA | clear |
| SPH-F-A12 | DMAc/2-MeTHF | clear |
| SPH-F-A13 | DMAc/CHCl₃ | clear |

Note:
THF:H₂O = 19:1, v/v.

The gas-liquid diffusion was performed under 13 kinds of experimental conditions, thereby obtaining crystal form B of SPH1772 ditartrate, and crystal form A of SPH1772 free base.

(7) Room-Temperature Solvent Evaporation Crystallization Experiment 15 mg crystal form A of SPH1772 ditartrate was added to a 3 mL vial, 1.5 mL-3.0 mL corresponding solvent or mixed solvent was added to prepare a clear solution, or to obtain a clear solution after filtration, the solution was sealed with a sealing membrane and placed at room temperature, punctured with 2 to 4 holes to evaporate naturally to give a solid.

TABLE 8 the solvent in the room-temperature solvent evaporation crystallization and the crystal form obtained

| Test number | Solvent (v:v) | Crystal form |
|---|---|---|
| SPH-G-A1 | THF | amorphous |
| SPH-G-A2 | 1,4-dioxane | crystal form B of SPH1772 ditartrate |
| SPH-G-A3 | 2-MeTHF | N/A |
| SPH-G-A4 | acetone/H₂O (9:4) | amorphous |
| SPH-G-A5 | THF/H₂O (19:1) | amorphous |

Note:
N/A refers to little solid.

The room-temperature solvent evaporation crystallization experiment was performed under 5 kinds of experimental conditions, thereby obtaining crystal form B of SPH1772 tartrate.

(8) Superpolymer-Induced Crystallization Experiment 15 mg compound was weighed and formulated into a saturated solution in the good solvent listed in Table 9, 1.5 to 3.0 mL per portion of the saturated solution was added to a 3 mL vial containing 2 mg corresponding mixed polymer. The mixture was sufficiently mixed by ultrasound, the vial was covered with a sealing membrane, punctured with a few holes on the sealing membrane, and the mixture was evaporated at room temperature, the solid was collected and characterized by XRPD. The result is shown in Table 9.

TABLE 9 the solvent in the superpolymer-induced crystallization experiment and the crystal form obtained

| Test number | Solvent (v:v) | Superpolymer | Crystal form |
|---|---|---|---|
| SPH-H-A1 | 1,4-dioxane | superpolymer A | crystal form B of SPH1772 ditartrate |
| SPH-H-A2 | 2-MeTHF | | amorphous |
| SPH-H-A3 | acetone/H₂O (9:4) | | amorphous |
| SPH-H-A4 | THF/H₂O (19:1) | | amorphous |
| SPH-H-A5 | 1,4-dioxane | superpolymer B | crystal form B of SPH1772 ditartrate |
| SPH-H-A6 | 2-MeTHF | | amorphous |
| SPH-H-A7 | acetone/H₂O (9:4) | | amorphous |
| SPH-H-A8 | THF/H₂O (19:1) | | crystal form B of SPH1772 ditartrate |

Note:
the mass ratio of superpolymer A: polyvinylpyrrolidone (PVP): polyvinyl alcohol (PVA): polyvinyl chloride (PVC): polyvinyl acetate (PVAC): hydroxypropyl methylcellulose (HPMC): methyl cellulose (MC) is 1:1:1:1:1:1. The mass ratio of superpolymer B: polycaprolactone (PCL): polyethylene glycol (PEG): polymethyl methacrylate (PMMA): sodium alginate (SA): hydroxyethyl cellulose (HEC) is 1:1:1:1:1.

The superpolymer-induced crystallization experiment was performed under 8 kinds of experimental conditions, thereby obtaining crystal form B of SPH1772 ditartrate.

In the present embodiments, according to XRPD result, four ditartrate crystal forms (A to D) were obtained, the identification result indicated that the crystal form A of SPH1772 ditartrate was anhydrous, the crystal form B and the crystal form C of SPH1772 ditartrate were disproportionation crystal form of SPH1772 ditartrate, the crystal form D of SPH1772 ditartrate was a DMSO solvate. Due to the possibly weak stability of crystal form B, crystal form C and crystal form D of SPH1772 ditartrate, crystal form A of SPH1772 ditartrate was the preferred crystal form. At the same time, crystal form A of SPH1772 monotartrate and crystal form B of SPH1772 were also obtained, crystal form A of SPH1772 monotartrate was anhydrous, and crystal form B of SPH1772 was a DMAc solvate.

The characterization data is as follows:

(1) Crystal Form A of SPH1772 Monotartrate

DSC showed a main endothermic peak at 209.2° C. Residual solvent: acetone, ethyl acetate—not detected. Melting point=202.1° C. ¹HNMR confirmed crystal form A of SPH1772 monotartrate.

¹HNMR (δppm, DMSO-d₆, 400 MHz) 9.22 (s, 1H), 9.18 (d, J=0.4 Hz, 1H), 8.64 (s, 1H), 8.46 (d, J=0.4 Hz, 1H), 8.37 (s, 1H), 8.31 (s, 1H), 8.07 (s, 1H), 7.99 (d, J=0.8 Hz, 1H), 7.84 (d, J=1.2 Hz, 1H), 7.76 (dd, J₁=8.4 Hz, J₂=2.0 Hz, 1H), 6.15 (s, 2H), 4.28 (s, 2H), 3.93 (s, 3H), 3.90 (s, 3H).

Figure 4:
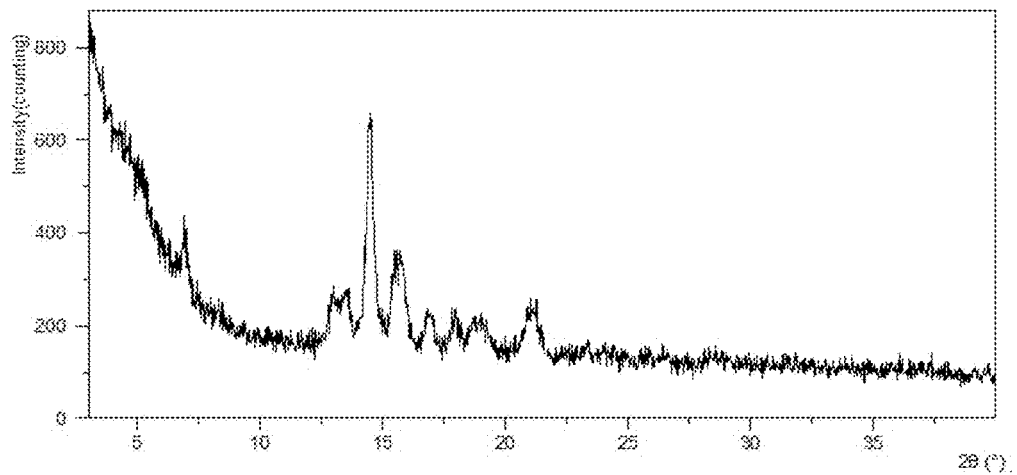
FIG. 4 is XRPD pattern of crystal form A of SPH1772 monotartrate.

The XRPD pattern is shown in FIG. 4, XPRD peaks are listed below:

| 2θ°[±0.2°] | Relative intensity % |
|---|---|
| 6.892 | 19.8 |
| 12.924 | 20.2 |
| 13.525 | 21.3 |

-continued

| 2θ°[±0.2°] | Relative intensity % |
|---|---|
| 14.512 | 100.0 |
| 15.639 | 37.3 |
| 16.990 | 14.4 |
| 17.912 | 14.9 |
| 19.098 | 11.0 |
| 21.024 | 18.9 |

(2) Crystal Form B of SPH1772

Melting point=263.2° C. DSC showed main endothermic peaks at 113.9° C., 171.7° C. and 268.8° C. Residual solvent: DMAc=51.5%. $^1$HNMR confirmed crystal form B of SPH1772.

$^1$HNMR (δppm, DMSO-$d_6$, 400 MHz) 9.22 (s, 1H), 9.17 (d, J=2.4 Hz, 1H), 8.64 (s, 1H), 8.46 (d, J=1.6 Hz, 1H), 8.37 (s, 1H), 8.31 (s, 1H), 8.07 (s, 1H), 7.99 (d, J=8.8 Hz, 1H), 7.84 (d, J=1.2 Hz, 1H), 7.76 (dd, $J_1$=8.4 Hz, $J_2$=2.0 Hz, 1H), 6.15 (s, 2H), 3.95 (s, 3H), 3.90 (s, 3H), 2.94 (s, 15H), 2.79 (s, 15H), 1.96 (s, 15H).

Figure 3:
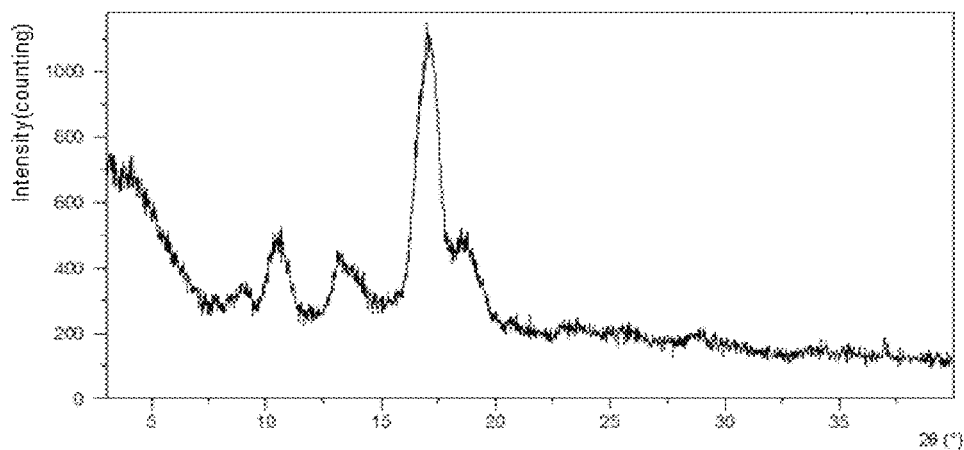
FIG. 3 is XRPD pattern of crystal form B of SPH1772.

The XRPD pattern is shown in FIG. 3, XPRD peaks are shown below:

| 2θ°[±0.2°] | Relative intensity % |
|---|---|
| 10.511 | 24.3 |
| 13.156 | 19.6 |
| 17.057 | 100.0 |
| 18.631 | 27.0 |
| 28.781 | 3.1 |

Effect Embodiment 1: Inhibitory Activity on c-Met Tyrosine Kinase Activity

Materials and Reagents:

c-Met kinase, purchased from Carna Biosciences, Inc. article No. 08-151;

Dimethyl sulfoxide, purchased from Sigma-Aldrich, article No. D8418;

ATP, purchased from Sigma-Aldrich, article No. A7699;

DTT solution, purchased from Sigma-Aldrich, article No. 43816;

EDTA solution, purchased from GIBCO, article No. 15575;

Test kit HTRF kinEASE-TK kit and related components, purchased from Cisbio Bioassays, wherein article No. of HTRF kinEASE-TK kit is 62TK0PEC;

96-well compound plate, purchased from Thermo Scientific, article No. 267245;

384-well plate, purchased from Greiner Bio-One, article No. 784075;

Other conventional chemical reagents were purchased from Sinopharm Chemical Reagent Co., Ltd.

The in vitro kinase assay uses Homogeneous Time-Resolved Fluorescence (HTRF) technology to screen the test compounds on the c-Met kinase at an ATP concentration of Km (wherein, Km represents the Michaelis constant, the unit is mol/L, which is the concentration of ATP at which the enzymatic reaction rate is half of the maximum reaction rate).

During the experiment, the initial concentration of the test compound was selected to be 111.11 nM, each compound set 10 serially diluted concentrations, the dilution-fold was 3-fold, each concentration set 2 duplicated wells, INCB28060 (Capmatinib) was used as a standard control.

All samples were formulated to a $10^{-2}$M stock solution using DMSO and stored in small quantities at −80° C. for use.

Experimental Method:

1, Preparing a 1× reaction buffer (the reaction buffer purchased was high-concentration, dilution was required when used, diluted to the final concentration required for the experiment, which was referred to as 1× reaction buffer.)

preparing 1× reaction buffer suitable for each kinase using 5× Enzymatic buffer in HTRF kinEASE-TK kit.

2, Preparing and transferring 5× compound (e.g. the final concentration of compound required for the experiment was 1 μm, then the concentration of the sample was first formulated to 5 μm, referred to as 5× compound.)

1) dilution of compound: Took 10 mM stock solution of the test compound, in a 96-well compound plate, DMSO was used to dilute the solution with multi-step to prepare 100× compound as an initial concentration, then this concentration was used as the first concentration, 3-fold diluted with DMSO was used to prepare 10 serial concentrations; 1 μL each serial dilution was then added to 19 μL 1× reaction buffer to prepare 5× compound for use;

2) transferring 5× compound: 2 μL 5× compound was transferred from 96-well plate to a 384-well plate; compound-free control well was added with 2 μL the following liquid: 19 μL 1× reaction buffer with an addition of 1 μL DMSO; 2 μL 250 mM EDTA was added to the Min control well.

In the present embodiment, the inhibitory activity data of the test compound on c-Met tyrosine kinase activity is shown in Table 10.

TABLE 10 the inhibitory activity data of the test compound on c-Met tyrosine kinase activity

| Compound | c-Met $IC_{50}$ (nM) |
|---|---|
| INCB28060 | 0.56 |
| crystal form A of SPH1772 ditartrate | 0.33 |
| crystal form A of SPH1772 | 0.27 |

The $IC_{50}$ of crystal form A of SPH1772 ditartrate and crystal form A of SPH1772 on inhibition of c-Met tyrosine kinase was lower than that of the positive reference compound INCB28060, which indicates that in vitro inhibitory activity was higher than INCB28060.

Effect Embodiment 2: Inhibitory Activity on the Proliferation of Human Lung Cancer H1993 Cell Materials and Reagents:

Cell Counting Kit-8 kit, purchased from Dojindo, article No. CK04;

H1993 human lung cancer cell, purchased from ATCC, article No. CRL-5909;

RPMI 1640, purchased from GIBCO, article No. 11875-093;

Strep/pen, purchased from GIBCO, article No. 15240-062;

Fetal bovine serum FBS, purchased from GIBCO, article No. 10099-141;

96-well cell culture plate, purchased from Corning, article No. 3599;

96-well compound plate, purchased from Thermo Scientific, article No. 267245;

Other conventional chemical reagents were purchased from Sinopharm Chemical Reagent Co., Ltd.

In the present embodiment, the Cell Counting Kit-8 (CCK-8) reagent was used to screen the compound SPH1772 and the salt thereof for inhibiting tumor cell proliferation against human lung cancer H1993 cell line, which was used to evaluate the in vitro inhibitory activity of the test compounds on this cell line.

CCK-8 is a kit for detecting cell proliferation, cell survival and cytotoxicity and an alternative method for the MTT method. During the experiment, the initial concentration of the test compound was selected to be 111.11 nM, each compound set 9 serially diluted concentrations, the dilution-fold was 3-fold, each concentration set 2 duplicated wells, INCB28060 (Capmatinib) was used as a standard control.

All samples were formulated to a $10^{-2}$ M stock solution with DMSO and stored in small quantities at $-80°$ C. for use.

Experimental Method:

1, Cell culture and inoculation: on the first day of the experiment, took normal cultured cells, when cells were in the exponential growth phase, the cells were dispersed by digesting and then inoculated in a 96-well cell culture plate at a density of $5.5 \times 10^4$ cells/mL (representing 55000 cells per mL), 90 μL per well; after completion of inoculation, the microplate was placed at 37° C. under 5% $CO_2$ condition overnight.

2, Dosing to cells: on the second day of the experiment, the microplate was taken out from incubator, 10× compound was added to each well of the microplate, 10 μL per well was added, each concentration set 2 duplicated wells, each compound had 9 dosing concentrations. According to different cell lines, the starting concentration of each compound was different.

3, Data acquisition: the compound and cells were incubated for 72 hours, the microplate containing the cells was taken out from incubator, 10 μL Cell Counting Kit-8 reaction solution was added to each well, and the microplate was placed in an incubator for 2-3 hours. The absorbance values were measured at 450 nm on the Flexstation 3 and set 650 nm as the reference wavelength.

4, In vitro inhibitory activity of the compound was calculated by the following formula: cell proliferation inhibition rate: inhibition rate (%)=(signal value of control-signal value of dosing)/signal value of control×100%. Based on the inhibition rate of each concentration, the LOG IT method was used to calculate 50% inhibitory concentration ($IC_{50}$).

TABLE 11 in vitro inhibitory activity of the test compound on the proliferation of H1993 cell line

| Compound | $IC_{50}$ (nM) |
| --- | --- |
| INCB28060 | 2.1 |
| crystal form A of SPH1772 ditartrate | 0.7 |
| crystal form A of SPH1772 | 0.5 |

The crystal form A of SPH1772 and crystal form A of SPH1772 ditartrate exhibit a better inhibitory activity on the proliferation of H1993 cells than the positive reference compound INCB28060, and a stronger inhibitory effect on the proliferation of H1993 cell line in vitro below nM level.

Effect Embodiment 3: Pharmacokinetic Study in Rats

Drugs, Animals and Reagents:

Analytical and animal experimental compounds were provided by Central Research Institute Pharmacy. Acetonitrile was HPLC pure reagent (Merck), formic acid (HCOOH) was HPLC pure reagent manufactured by CNW. Other analytical pure organic reagents were provided by Sinopharm (Group) Shanghai Chemical Reagent Co., Ltd. Analytical pure water was prepared from deionized water via MilliQ water purification system.

SD rats, male, 180-200 g, provided by Shanghai Sciple Rubicam Ex Animal Co., Ltd.

Experimental Instruments: liquid chromatography/mass spectrometry analysis system (LC/MS/MS) was consisted of Waters AcQuity UPLC in serial connection to API 4000 Q-trap mass spectrometer detector.

Experimental Method:

All stock solutions of the test compound were sonicated and heated to become clarified and formulated to a 25 mM solution with DMSO.

All samples were dosed at 20 μmol/kg.

SD rats were divided into 3 groups (three rats per group), the rats were dosed by intragastrical administration with crystal form A of SPH1772 ditartrate, crystal form A of SPH1772 and INCB28060 hydrochloride (8 mL/kg, 2.5 mM) at a dose of 20 μmol/kg, respectively. Blood samples (about 0.4 mL at each time point) were collected through the ophthalmic venous plexus before intragastrical administration and 5, 15, 30, 60, 90, 120, 240, 360, 480, 720, and 1440 min after intragastrical administration, respectively. The blood sample was centrifuged at 8000 rpm for 5 min, the plasma was collected in a centrifuge tube and stored at $-20°$ C. for use.

Treatment of the plasma sample: the proteins in 50 μL plasma sample were precipitated with 200 μL acetonitrile containing internal standard (Propranolol (PRO), 2.5 ng/mL). Vortexed for 10 min, centrifuged at 6000 g for 10 min, the supernatant was taken and 5-fold diluted with the mobile phase, and the supernatant was injected into a 96-well plate for analysis.

Measurement Method of Sample:

1, Instruments

Liquid chromatography system: Acquity UPLC liquid chromatography system (including binary infusion pump, autosampler, column oven, degasser), Waters Corporation, USA.

MS/MS System: API 4000 Q-Trap Triple Quadrupole Mass Spectrometer with Electrospray Ionization (ESI), Applied Biosystems, USA.

Data acquisition: Analyst 1.5.1 software, Applied Biosystems, USA.

2, Conditions of LC

Analytical column: BEH C18 column, 1.7 μm particle size, 50×2.1 mm I.D., Waters Corporation, US.

flow rate: 0.3 mL/min; injection volume: 2 μL; column temperature 45° C. The gradient elution procedure was:

| Time (min) | A (1 MmNH$_4$FA-0.025% FA-H$_2$O) | B (1 MmNH$_4$FA-0.025% FA-METH) |
| --- | --- | --- |
| 0 | 95% | 5% |
| 0.5 | 95% | 5% |
| 1 | 5% | 95% |
| 2 | 5% | 95% |
| 2.5 | 95% | 5% |
| 3 | 95% | 5% |

3, Conditions of MS

The ion source was an electrospray ionization source (Turbo Ionspray, ESI); the electrospray voltage was 5500V; the temperature was 500° C.; pressure of ion source gas 1 ($N_2$) was 50 psi; pressure of ion source gas 2 ($N_2$) was 50 psi; pressure of curtain gas (N₂) 20 psi; pressure of collision gas (CAD) was Medium; scan time was 100 ms; positive ion mode detection; scan mode was multiple reaction monitoring (MRM), ion reaction and collision energy (CE) for quantitative analysis, declustering potential (DP) are shown in the following table:

| Compound | Parent | product | DP | CE |
|---|---|---|---|---|
| Propranolol | 260.1 | 116 | 76 | 26 |
| SPH1772 | 423.2 | 222.1 | 60 | 23 |
| INCB28060 hydrochloride | 413.2 | 382.1 | 100 | 35 |

Figure 5:
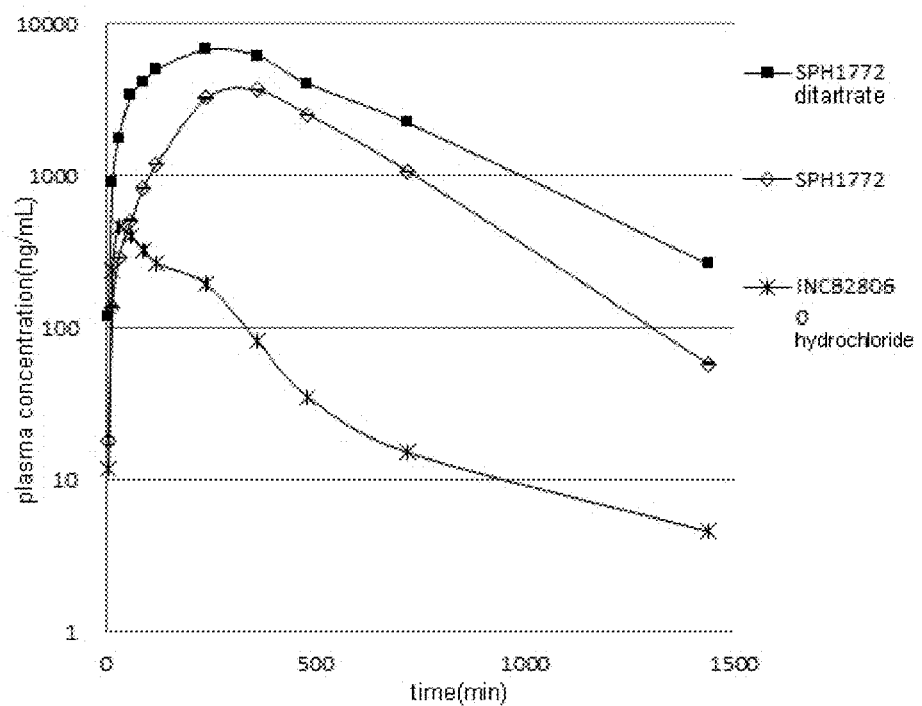
FIG. 5 is a drug concentration-time curve of test compound in rat obtained in Effect embodiment 3.
Figure 6:
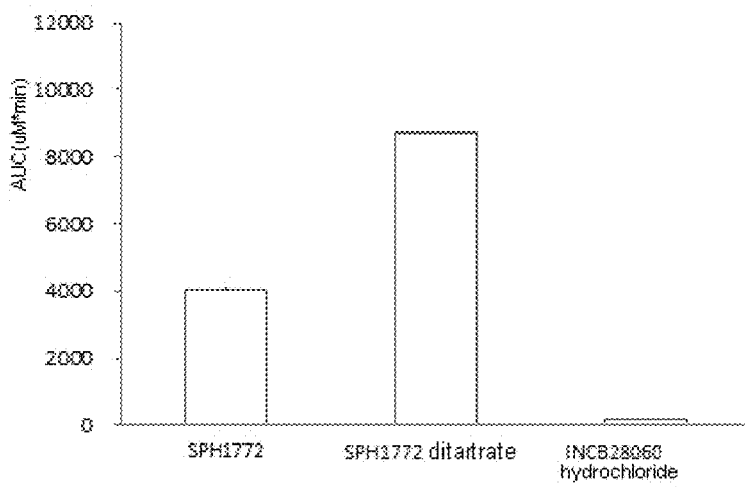
FIG. 6 is histogram of area under the curve of test compound in rat obtained in Effect embodiment 3.
Figure 7:
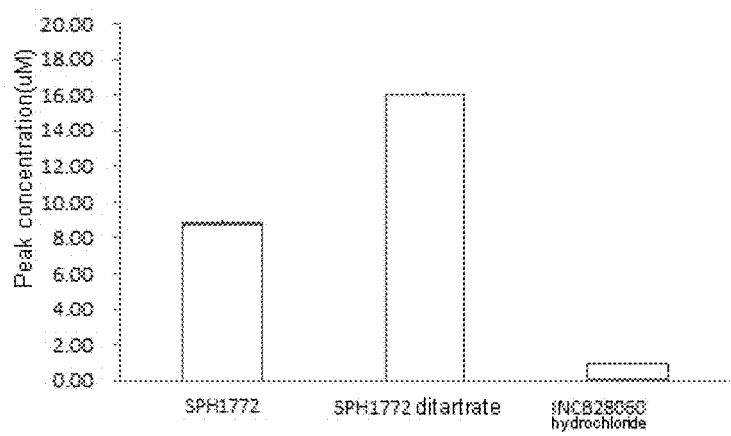
FIG. 7 is histogram of peak concentration of test compound in rat obtained in Effect embodiment 3.

The linear range of the standard curve of SPH1772 in rat plasma was 0.01 to 22.5 μM, the lower limit of quantitation was 0.01 μM. The linear range of the standard curve of INCB28060 hydrochloride in rat plasma was 0.002 to 5 μM, the lower limit of quantification was 0.002 μM. In vivo pharmacokinetic parameters of the crystal form A of SPH1772 ditartrate, crystal form A of SPH1772 and INCB28060 hydrochloride were shown in Tables 12 to 14. The drug concentration-time curve of the test compound in rats is shown in FIG. 5, and the histogram of area under the curve (AUC(0-t)) of the test compound in rats is shown in FIG. 6; the histogram of the peak concentration (Cmax) of the test compound in rats is shown in FIG. 7.

TABLE 12

Plasma concentration of crystal form A of SPH1772 ditartrate in rats

| Time | Plasma concentration (μM) | | | Mean | Standard |
|---|---|---|---|---|---|
| (min) | Rat1 | Rat 2 | Rat 3 | (μM) | deviation |
| 5 | 0.251 | 0.157 | 0.403 | 0.27 | 0.12 |
| 15 | 1.94 | 1.34 | 2.93 | 2.07 | 0.80 |
| 30 | 4.18 | 2.56 | 5.36 | 4.03 | 1.41 |
| 60 | 6.67 | 9.67 | 7.16 | 7.83 | 1.61 |
| 90 | 8.95 | 10.9 | 8.59 | 9.48 | 1.24 |
| 120 | 11.3 | 14.3 | 9.01 | 11.54 | 2.65 |
| 240 | 17.5 | 12.9 | 16.3 | 15.57 | 2.39 |
| 360 | 14.9 | 12.8 | 14.8 | 14.17 | 1.18 |
| 480 | 8.81 | 7.72 | 11.5 | 9.34 | 1.95 |
| 720 | 4.73 | 4.14 | 6.42 | 5.10 | 1.18 |
| 1440 | 0.581 | 0.377 | 0.85 | 0.60 | 0.24 |

TABLE 13

Plasma concentration of crystal form A of SPH1772 in rats

| Time | Plasma concentration (μM) | | | Mean | Standard deviation |
|---|---|---|---|---|---|
| (min) | Rat1 | Rat 2 | Rat 3 | (μM) | SD |
| 5 | 0.0466 | 0.0589 | 0.0196 | 0.04 | 0.02 |
| 15 | 0.345 | 0.547 | 0.0526 | 0.31 | 0.25 |
| 30 | 0.834 | 0.982 | 0.153 | 0.66 | 0.44 |
| 60 | 1.4 | 1.77 | 0.327 | 1.17 | 0.75 |
| 90 | 2.45 | 2.86 | 0.449 | 1.92 | 1.29 |
| 120 | 3.68 | 3.91 | 0.538 | 2.71 | 1.88 |
| 240 | 8.06 | 13.2 | 1.22 | 7.49 | 6.01 |
| 360 | 6.67 | 17.1 | 1.56 | 8.44 | 7.92 |
| 480 | 3.28 | 13.3 | 0.922 | 5.83 | 6.57 |
| 720 | 1.38 | 5.78 | 0.228 | 2.46 | 2.93 |
| 1440 | 0.195 | 0.185 | 0.0208 | 0.13 | 0.10 |

TABLE 14

Plasma concentration of crystal form A of INCB28060 hydrochloride in rats

| Time | Plasma concentration (μM) | | | Mean | Standard deviation |
|---|---|---|---|---|---|
| (min) | Rat1 | Rat 2 | Rat 3 | (μM) | SD |
| 5 | 0.0153 | 0.0425 | 0.0222 | 0.03 | 0.01 |
| 15 | 0.399 | 0.732 | 0.448 | 0.53 | 0.18 |
| 30 | 0.784 | 1.32 | 0.99 | 1.03 | 0.27 |
| 60 | 0.616 | 1.21 | 0.897 | 0.91 | 0.30 |
| 90 | 0.394 | 0.961 | 0.835 | 0.73 | 0.30 |
| 120 | 0.305 | 0.725 | 0.758 | 0.60 | 0.25 |
| 240 | 0.465 | 0.333 | 0.495 | 0.43 | 0.09 |
| 360 | 0.193 | 0.148 | 0.211 | 0.18 | 0.03 |
| 480 | 0.0885 | 0.042 | 0.107 | 0.08 | 0.03 |
| 720 | 0.0626 | 0.0131 | 0.0257 | 0.03 | 0.03 |
| 1440 | 0.00808 | 0.00699 | 0.0156 | 0.01 | 0.00 |

TABLE 15

In vivo pharmacokinetic data of the test compound in rats

| | | crystal form A of SPH1772 ditartrate | crystal form A of SPH1772 | INCB28060 hydrochloride |
|---|---|---|---|---|
| AUC(0-t) | uM*min | 8802.13 | 4057.55 | 223.81 |
| AUCextra | uM*min | 210.83 | 36.83 | 4.29 |
| AUCtot | uM*min | 9012.96 | 4094.37 | 228.10 |
| thalf | min | 236.71 | 185.79 | 283.79 |
| MRT | min | 473.59 | 448.80 | 271.69 |
| Clearance | L/min/kg | 0.002 | 0.013 | 0.089 |
| Vz | L/kg | 0.760 | 3.448 | 35.978 |
| $V_{ss}$ | L/kg | 1.053 | 5.688 | 24.325 |
| $C_{max}$ | uM | 16.03 | 8.91 | 1.03 |
| $T_{max}$ | min | 200.00 | 320.00 | 30.00 |
| Dose | umol/kg | 20.00 | 20.00 | 20.00 |

As shown in the table, when the dose was 20 μmol/Kg, the AUC(0-24 h) of crystal form A of SPH1772 was 4057.55 μM*min, the AUC (0-24 h) of crystal form A of SPH1772 ditartrate was 8802.13 μM*min. Compared to crystal form A of SPH1772, the AUC value of crystal form A of SPH1772 ditartrate was increased by 2.17 times, and Cmax was increased by 1.80 times. At the same dose, crystal form A of SPH1772 ditartrate exhibit better pharmacokinetic properties than crystal form A of SPH1772. Overall, the exposure of INCB28060 hydrochloride in rats was not as good as that of crystal form A of SPH1772 ditartrate and crystal form A of SPH1772.

Effect Embodiment 4: Evaluation of Anti-Tumor Effect of Crystal Form A of SPH1772 Ditartrate on Human Hepatoma MHCC97H Cell Line in BALB/c Nude Mice Xenograft Model 4.1 Experimental Method BALB/c nude mice were subcutaneously inoculated with MHCC97H cells to develop human hepatocellular carcinoma subcutaneously transplanted tumor model. The experiment was divided into groups including crystal form A of SPH1772 ditartrate (0.05 mg/kg, 0.5 mg/kg and 5 mg/kg), positive control INC280 hydrochloride (5 mg/kg), and Vehicle control group, 10 mice in each group, intragastric administration once a day, lasting 21 days. The efficacy was according to the relative tumor inhibition rate (TGI) and tumor growth delay time, the safety was evaluated according to animal weight and death.

4.2 Experimental Animals

BALB/c nude mice, female, 7 to 9 weeks old (the age when mice were inoculated with tumor cells), weight 19.5 to 23.9 g, 75 animals. BALB/c nude mice were purchased from Shanghai Lingchang Biotechnology Co., Ltd., animal certificate number: 2013001816956. Rearing environment: SPF level.

4.3 Cells and Related Reagents

MHCC97H (Zhongshan Hospital subsidiary to Fudan University) was cultured in DMEM containing 10% fetal bovine serum. MHCC97H cells were collected during exponential growth phase, the cells in PBS was re-suspended to a suitable concentration for subcutaneous tumor inoculation in mice.

4.4 Animal Modeling and Grouping 0.2 mL 1×10$^7$ MHCC97H cells re-suspended in PBS and Matrigel (1:1) was subcutaneously inoculated to the right side of 75 mice. When the mean tumor volume reached 157 mm$^3$, mice were randomly grouped based on tumor volume. The formula for calculating the tumor volume was that long diameter×short diameter$^2$/2.

4.5 Standard of Result Judgment

Relative tumor inhibition rate TGI (%): TGI=1−T/C (%). T/C % is the relative tumor proliferation rate, which is the percentage of the relative tumor volume or tumor weight in the treatment group to that of the control group at a certain time. T and C are respectively the relative tumor volume (RTV) or tumor weight (TW) of the treatment group and control group at a certain time.

The formula was as follows: T/C %=$T_{RTV}/C_{RTV}$*100% ($T_{RTV}$: mean RTV in the treatment group; $C_{RTV}$: mean RTV in the control group; RTV=$V_t/V_0$, $V_0$ was the tumor volume of the animal when grouped, and Vt was the tumor volume of the animal after treatment). Or T/C %=$T_{TW}/C_{TW}$×100% ($T_{TW}$: mean tumor weight in the treatment group at the end of the experiment; $C_{TW}$: mean tumor weight in the control group at the end of experiment).

4.6 Experimental Endpoint 1.5 h and 24 h after the last dose, blood and tumor were collected, the tumor was weighted, and photographs were taken.

4.7 Statistical Analysis

All experimental results were expressed as mean tumor volume±SEM (mean standard error). Statistical analysis between different groups was performed on the best point of drug treatment (usually after the last dosing). The independent sample T test method was used to evaluate whether there was significant difference between the relative tumor volume and tumor weight in the treatment group to that of the control group. All data was analyzed by SPSS 18.0. p<0.05 was considered having significant differences.

4.8 Experimental Results

Figure 8:
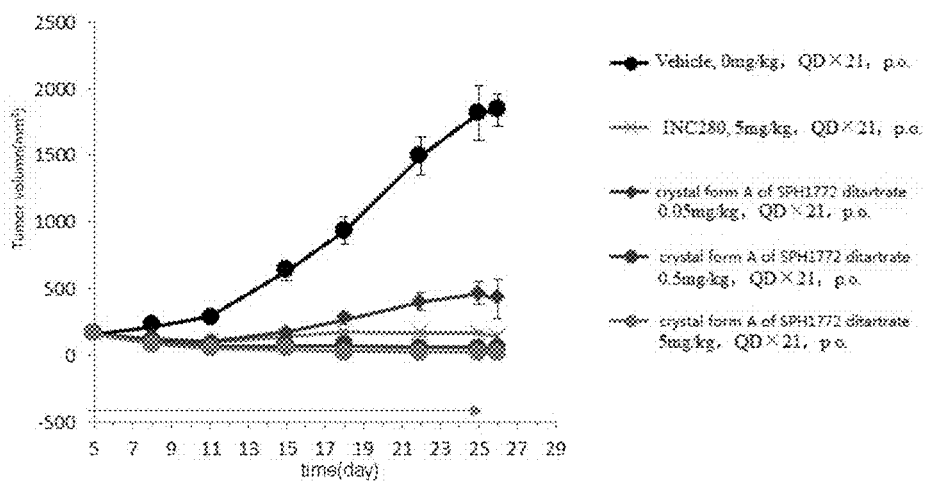
FIG. 8 is a growth curve of tumor volume in mice of each treatment group and control group in MHCC97H human hepatoma model.

The mean tumor volume of mice at the 25th day after dosing in the menstruum control group was 1815 mm$^3$. The mean tumor volume at the 25th day after dosing in the treatment group of crystal form A of SPH1772 ditartrate (0.05 mg/kg) was 469 mm$^3$, the relative tumor inhibition rate TGI (%) was 74%. The mean tumor volume at the 25th day after dosing in the treatment group of crystal form A of SPH1772 ditartrate (0.5 mg/kg) was 60 mm$^3$, the relative tumor inhibition rate TGI (%) was 97%. The mean tumor volume at the 25th day after dosing in the treatment group of crystal form A of SPH1772 ditartrate (5 mg/kg) was 22 mm$^3$, the relative tumor inhibition rate TGI (%) was 99%. The mean tumor volume at the 25th day after dosing in the treatment group of INC280 (5 mg/kg) was 166 mm$^3$, the relative tumor inhibition rate TGI (%) was 91%. The tumor weight analysis result was basically consistent with the result of the relative tumor volume analysis. The tumor growth in each treatment group and control group is shown in Table 16, Table 17 and FIG. 8.

TABLE 16

TGI, T/C on MHCC97H human hepatocellular carcinoma model in each group

| Experimental group | 25th day after dosing | | | | |
|---|---|---|---|---|---|
| | tumor volume ($\bar{x} \pm S$) | relative tumor volume ($\bar{x} \pm S$) | TGI (%) | T/C (%) | P Value (compared to control group) |
| 1th group Vehicle 0 mg/kg | 1815 ± 206 | 11.71 ± 1.30 | — | — | — |
| 2th group INC280 5 mg/kg | 166 ± 17 | 1.05 ± 0.09 | 91 | 9 | <0.001 |
| 3th group crystal form A of SPH1772 ditartrate 0.05 mg/kg | 469 ± 85 | 3.03 ± 0.56 | 74 | 26 | <0.001 |
| 4th group crystal form A of SPH1772 ditartrate 0.5 mg/kg | 60 ± 5 | 0.39 ± 0.03 | 97 | 3 | <0.001 |
| 5th group crystal form A of SPH1772 ditartrate 5 mg/kg | 22 ± 3 | 0.14 ± 0.02 | 99 | 1 | <0.001 |

TABLE 17 tumor weight in each group

| Group | Tumor weight (mg) ($\bar{x} \pm s$) 26th day after dosing | TGI (%) | P value (compared to control group) |
|---|---|---|---|
| Vehicle (0 mg/kg) | 1586 ± 131 | — | — |
| INC280 (5 mg/kg) | 136 ± 19 | 91 | <0.001 |
| crystal form A of SPH1772 ditartrate (0.05 mg/kg) | 493 ± 71 | 69 | <0.001 |
| crystal form A of SPH1772 ditartrate (0.5 mg/kg) | 48 ± 2 | 97 | <0.001 |
| crystal form A of SPH1772 ditartrate (5 mg/kg) | 31 ± 3 | 98 | <0.001 |

In the treatment group of crystal form A of SPH1772 ditartrate on MHCC97H human hepatoma model described above, no animal died, no significant drug toxicity was exhibit, and they were well tolerated during the treatment period.

Effect embodiment 5: Evaluation of anti-tumor effect of crystal form A of SPH1772 ditartrate on patient-derived lung tumor xenograft model LU2503

5.1 Model Information

A HuPrime® female patient-derived lung tumor xenograft model LU2503 was used for this pharmacodynamic experiment. There was an exon 14 deletion in of MET gene in this model. At the same time, the model had a slight cachexia and tended to have a tendency of tumor collapse.

5.2 Experimental Method

Tumor tissue was harvested from HuPrime® lung tumor xenograft model LU2503 (R11P6) tumor-bearing mice and cut into 2 to 3 mm diameter tumor blocks subcutaneously inoculated at the right anterior scapular of BALB/c nude mice. When the mean tumor volume reached approximately 139 mm$^3$, mice were randomly divided to 6 experimental groups based on tumor volume, 8 mice in each group, 4 mice per cage. The day of grouping was defined as day 0. Dosing started on day 0 and ended on day 20. The experiment ended on the 21st day. The experiment was divided into groups of crystal form A of SPH1772 ditartrate (0.3 mg/kg, 3 mg/kg and 30 mg/kg), positive control INC280 (30 mg/kg), positive control Crizotinib (30 mg/kg) and vehicle group, 8 mice in each group, intragastric administration once a day, lasting 21 days.

5.3 Experimental Animals

BALB/c nude mice, female, 8 to 9 weeks old (the age when mice were inoculated with tumor cells), 52 animals. BALB/c nude mice were purchased from Nanjing Biomedical Research Institute of Nanjing University, License number: SCXK (Su) 2015-0001; Quality certification number: 201602064. Rearing environment: SPF level.

5.4 Animal Grouping

When the mean tumor volume reached 139 mm$^3$, mice were randomly grouped based on tumor volume. The formula for calculating the tumor volume was that long diameter×short diameter$^2$/2.

5.5 Standard of Result Judgment Refers to 4.5

5.6 Experimental Endpoint Refers to 4.6

5.7 Statistical Analysis Refers to 4.7

5.8 Experimental Results

On the 21th day after grouping and treatment, weight change percentage of tumor-bearing mice in the 1st group (INC280, 30 mg/kg, QD*21), 2nd group (vehicle, QD*21), 3rd group (crystal form A of SPH1772 ditartrate, 0.3 mg/kg, QD*21), 4th group (crystal form A of SPH1772 ditartrate, 3 mg/kg, QD*21), 5th group (crystal form A of SPH1772 ditartrate, 30 mg/kg, QD*21) and 6th group (Crizotinib, 30 mg/kg, QD*21) was −5.00%, −9.86%, −1.61%, −1.88%, −2.01% and 3.26%, respectively.

Figure 9:
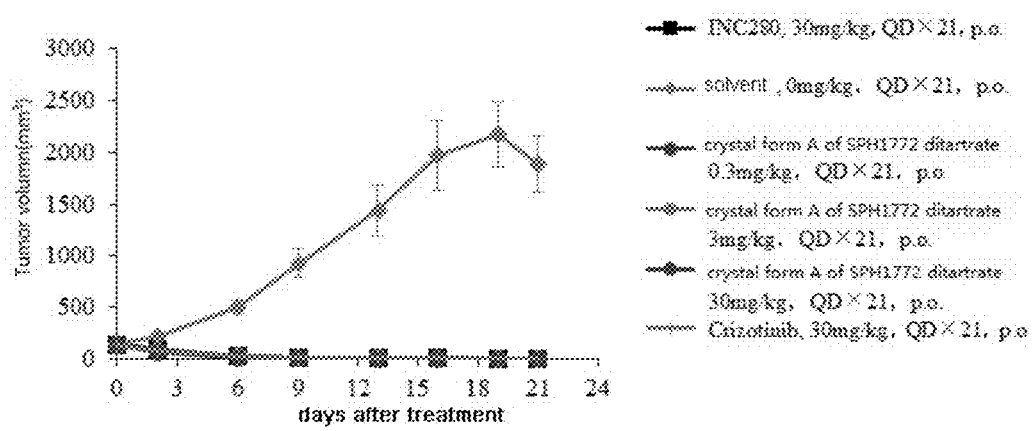
FIG. 9 is a growth curve of tumor volume in mice of each treatment group and control group in LU2503 human lung tumor model.

On the 21th day after grouping and treatment, the mean tumor volume of the vehicle group reached 1886.32 mm$^3$. The tumor in other groups completely regressed, the relative tumor proliferation rate (T/C %) was all 0.00%, having statistically significant effect on anti-LU2503 tumor growth (P<0.05). The tumor volume of tumor-bearing mice in each treatment group and vehicle group at different time is shown in Table 18, Table 19 and FIG. 9.

TABLE 18

Tumor volume of tumor-bearing mice in each treatment group and vehicle group

| Days after treatment | 1st group INC280 30 mg/kg | 2nd group vehicle — | 3rd group crystal form A of SPH1772 ditartrate 0.3 mg/kg | 4th group crystal form A of SPH1772 ditartrate 3 mg/kg | 5th group crystal form A of SPH1772 ditartrate 30 mg/kg | 6th group Crizotinib 30 mg/kg |
|---|---|---|---|---|---|---|
| 0 | 139.14 ± 19.30 | 139.13 ± 17.81 | 139.09 ± 19.03 | 138.85 ± 16.77 | 138.93 ± 18.13 | 138.99 ± 18.22 |
| 2 | 86.20 ± 6.49 | 216.85 ± 27.34 | 71.49 ± 9.02 | 74.25 ± 7.03 | 67.62 ± 8.13 | 78.65 ± 7.77 |
| 6 | 23.03 ± 4.10 | 495.06 ± 68.25 | 22.13 ± 2.10 | 24.04 ± 2.67 | 13.38 ± 2.67 | 21.63 ± 2.93 |
| 9 | 10.55 ± 1.97 | 928.64 ± 143.77 | 15.19 ± 2.89 | 9.15 ± 2.23 | 6.07 ± 1.65 | 12.83 ± 2.68 |
| 13 | 5.89 ± 1.81 | 1433.91 ± 245.76 | 8.95 ± 0.91 | 4.78 ± 1.56 | 2.19 ± 1.44 | 8.30 ± 2.08 |
| 16 | 5.07 ± 1.99 | 1972.58 ± 339.36 | 6.22 ± 1.65 | 2.25 ± 1.47 | 0.00 ± 0.00 | 8.27 ± 2.55 |
| 19 | 1.53 ± 1.53 | 2176.65 ± 314.52 | 0.00 ± 0.00 | 0.00 ± 0.00 | 0.00 ± 0.00 | 2.77 ± 2.77 |
| 21 | 0.00 ± 0.00 | 1886.32 ± 271.80 | 0.00 ± 0.00 | 0.00 ± 0.00 | 0.00 ± 0.00 | 2.11 ± 2.11 |

Note:
Data was expressed as "mean ± standard error".

TABLE 19

Tumor inhibitory effect on HuPrime ® lung tumor xenograft model LU 2503

| Group | Treatment | Day 0 tumor volume$^a$ (mm$^3$) | 21th day tumor volume$^a$ (mm$^3$) | RTV | T/C (RTV) (%) | TGI (%) | P value$^b$ |
|---|---|---|---|---|---|---|---|
| 1 | INC280, 30 mg/kg, PO, QD × 21 | 139.14 ± 19.30 | 0.00 ± 0.00 | 0.00 | 0.00 | 107.96 | 0.018 |
| 2 | vehicle, PO, QD × 21 | 139.13 ± 17.81 | 1886.32 ± 271.80 | 13.56 | — | — | — |
| 3 | crystal form A of SPH1772 ditartrate, 0.3 mg/kg, PO, QD × 21 | 139.09 ± 19.03 | 0.00 ± 0.00 | 0.00 | 0.00 | 107.96 | 0.018 |

TABLE 19-continued

Tumor inhibitory effect on HuPrime ® lung tumor xenograft model LU 2503

| Group | Treatment | Day 0 tumor volume[a] (mm³) | 21th day tumor volume[a] (mm³) | RTV | T/C (RTV) (%) | TGI (%) | P value[b] |
|---|---|---|---|---|---|---|---|
| 4 | crystal form A of SPH1772 ditartrate, 3 mg/kg, PO, QD × 21 | 138.85 ± 16.77 | 0.00 ± 0.00 | 0.00 | 0.00 | 107.95 | 0.018 |
| 5 | crystal form A of SPH1772 ditartrate, 30 mg/kg, PO, QD × 21 | 138.93 ± 18.13 | 0.00 ± 0.00 | 0.00 | 0.00 | 107.95 | 0.018 |
| 6 | Crizotinib, 30 mg/kg, PO, QD × 21 | 138.99 ± 18.22 | 2.11 ± 2.11 | 0.02 | 0.11 | 107.83 | 0.018 |

In this study, crystal form A of SPH1772 ditartrate was used in monotherapy and had statistically significant effect on growth of anti-HuPrime® lung tumor xenograft model LU2503 at a dose of 0.3 mg/kg, 3 mg/kg, and 30 mg/kg. At the same dose, the effect of crystal form A of SPH1772 ditartrate on growth of anti-HuPrime® lung tumor xenograft model LU2503 was equivalent to that of INC280 and Crizotinib.

It is to be understood that the foregoing description of two preferred embodiments is intended to be purely illustrative of the principles of the invention, rather than exhaustive thereof, and that changes and variations will be apparent to those skilled in the art, and that the present invention is not intended to be limited other than expressly set forth in the following claims.

What is claimed is:

1. A crystal form A of the quinoline compound SPH1772 ditartrate, having an X-ray powder diffraction pattern represented by diffraction angle 2θ comprising characteristic peaks at 7.5±0.2°, 9.2±0.2°, 14.5±0.2°, 16.6±0.2°, 20.3±0.2° and 28.8±0.2°; the target used in the X-ray powder diffraction is Cu target;

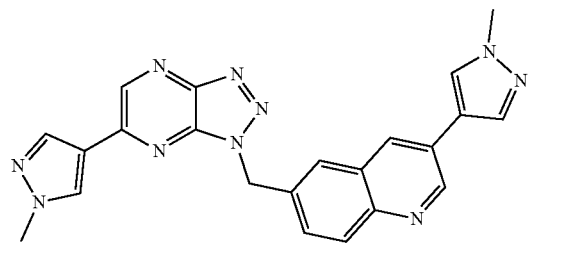

SPH1772 ditartrate

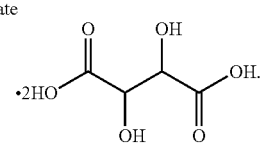

wherein the tartaric acid is L-tartaric acid.

2. The crystal form A of the quinoline compound SPH1772 ditartrate according to claim 1, wherein the melting point of the crystal form A of SPH1772 ditartrate is 202° C., and/or, the DSC of the crystal form A of SPH1772 ditartrate has a main endothermic peak at 199.4° C.

3. A preparation method for the crystal form A of the quinoline compound SPH1772 ditartrate according to claim 1, comprising that in an organic solvent, the compound SPH1772 reacts with tartaric acid; wherein the organic solvent is ethyl acetate.

4. The preparation method according to claim 3, wherein the volume/mass ratio of the organic solvent to the SPH1772 is 40 mL/g to 80 mL/g;

and/or, the molar ratio of SPH1772 to the tartaric acid is 1:2.0 to 1:2.2;

and/or, the reaction temperature is 40 to 60° C.;

and/or, the reaction time is 24 h to 72 h;

and/or, the preparation method for the crystal form A of SPH1772 ditartrate comprises adding the tartaric acid to "mixture of the compound SPH1772 and the organic solvent";

and/or, the preparation method for the crystal form A of SPH1772 ditartrate, after the completion of the reaction, further comprises that the reaction solution is filtered to give the crystal form A of SPH1772 ditartrate.

5. The preparation method according to claim 3, wherein the volume/mass ratio of the organic solvent to SPH1772 is 60 to 70 mL/g;

and/or, the molar ratio of SPH1772 to the tartaric acid is 1:2.1;

and/or, the reaction temperature is 50° C.;

and/or, the reaction time is 24 h to 48 h;

and/or, when the tartaric acid participates in the reaction in the form of a "solution of tartaric acid in the organic solvent", in the "solution of tartaric acid in the organic solvent", the volume/molar ratio of the organic solvent to the tartaric acid is 3.5:1 to 4.5:1 mL/mmol;

and/or, when the tartaric acid participates in the reaction in the form of a "solution of tartaric acid in the organic solvent", the addition rate of the "solution of tartaric acid in the organic solvent" is 1 to 5 mL/min.

6. A method for inhibiting tyrosine kinase c-Met, comprising administering an effective amount of the crystal form A of SPH1772 ditartrate according to claim 1 to the subject.

7. A composition, comprising the crystal form A of SPH1772 ditartrate according to claim 1 and a pharmaceutically acceptable excipient.

8. The crystal form A of the quinoline compound SPH1772 ditartrate according to claim 1, wherein the crystal form A has an X-ray powder diffraction pattern represented by diffraction angle 2θ comprising characteristic peaks at the values as shown in the following table:

| 2θ° [±0.2°] |
| --- |
| 7.089 |
| 7.541 |
| 9.150 |
| 11.019 |
| 14.163 |
| 14.545 |
| 16.589 |
| 17.130 |
| 17.825 |
| 19.752 |
| 20.283 |
| 21.389 |
| 21.598 |
| 22.783 |
| 23.161 |
| 25.314 |
| 25.789 |
| 26.670 |
| 26.927 |
| 28.264 |
| 28.758 |
| 29.348 |
| 31.248 |
| 32.305 |
| 33.048 |
| 33.842 |
| 35.343 |
| 38.305. |

9. The preparation method according to claim 5, wherein
when the tartaric acid participates in the reaction in the form of a "solution of tartaric acid in the organic solvent", in the "solution of tartaric acid in the organic solvent", the volume/molar ratio of the organic solvent to the tartaric acid is 4:1 mL/mmol;

and/or, when the tartaric acid participates in the reaction in the form of a "solution of tartaric acid in the organic solvent", the addition rate of the "solution of tartaric acid in the organic solvent" is 2.5 mL/min.

* * * * *